United States Patent
Ji et al.

(10) Patent No.: US 8,338,424 B2
(45) Date of Patent: *Dec. 25, 2012

(54) GUANIDINE-CONTAINING COMPOUNDS USEFUL AS MUSCARINIC RECEPTOR ANTAGONISTS

(75) Inventors: YuHua Ji, Redwood City, CA (US); Craig Husfeld, Redwood City, CA (US); YongQi Mu, Los Altos, CA (US); Rick Lee, Daly City, CA (US); Li Li, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/468,200

(22) Filed: May 10, 2012

(65) Prior Publication Data

US 2012/0219509 A1 Aug. 30, 2012

Related U.S. Application Data

(60) Continuation of application No. 13/228,782, filed on Sep. 9, 2011, now Pat. No. 8,198,304, which is a division of application No. 13/096,651, filed on Apr. 28, 2011, now Pat. No. 8,039,489, which is a division of application No. 12/231,861, filed on Sep. 5, 2008, now Pat. No. 7,960,385.

(60) Provisional application No. 60/967,914, filed on Sep. 7, 2007.

(51) Int. Cl.
*A61K 31/496* (2006.01)

(52) U.S. Cl. .............. 514/252.13; 514/254.1; 544/379

(58) Field of Classification Search ............ None
See application file for complete search history.

(56) References Cited

U.S. PATENT DOCUMENTS

| | | | |
|---|---|---|---|
| 3,732,247 A | 5/1973 | Helsley et al. |
| 5,070,087 A | 12/1991 | Teng et al. |
| 6,140,333 A | 10/2000 | Tsuchiya et al. |
| 6,693,202 B1 | 2/2004 | Aggen et al. |
| 6,846,835 B2 | 1/2005 | Ogino et al. |
| 7,122,558 B2 | 10/2006 | Quinones et al. |
| 7,192,978 B2 | 3/2007 | Quinones et al. |
| 7,834,185 B2 | 11/2010 | Ji et al. |
| 8,017,617 B2 | 9/2011 | Ji et al. |
| 2003/0055080 A1 | 3/2003 | Forner et al. |
| 2006/0287362 A1 | 12/2006 | Collingwood et al. |
| 2007/0060563 A1 | 3/2007 | Collingwood et al. |
| 2008/0269190 A1 | 10/2008 | Husfeld et al. |

FOREIGN PATENT DOCUMENTS

| | | |
|---|---|---|
| EP | 0309422 A2 | 3/1989 |
| EP | 0309424 A1 | 3/1989 |
| EP | 0930298 A1 | 7/1999 |
| EP | 1302458 A1 | 4/2003 |
| WO | 01/042212 A1 | 6/2001 |
| WO | 03/087096 A1 | 10/2003 |
| WO | 2004/056767 A1 | 7/2004 |
| WO | 2005/090342 A1 | 9/2005 |
| WO | 2006/005980 A1 | 1/2006 |
| WO | 2006/048225 A1 | 5/2006 |
| WO | 2006/066928 A1 | 6/2006 |
| WO | 2006/066929 A1 | 6/2006 |
| WO | 2007/017669 A1 | 2/2007 |
| WO | 2007/017670 A1 | 2/2007 |

OTHER PUBLICATIONS

Biel et al., Central Stimulants II, 26:4096-4103 (1961).
Mitsuya et al., "A potent, long-acting, orally active (2R)-2-[(1R)-3,3-difluorocyclopentyl]-2-hydroxy-2-phenylacetamide: A novel muscarinic M3 receptor antagonist with high selectivity for M3 over M2 receptors", Journal of Medicinal Chemistry, 43(26):5017-5029 (2000).
Ogino et al., "Muscarinic M3 receptor antagonists with (2R)-2-[(1R)-3,3-difluorocyclopentyl]. . .", Bioorganic & Medicinal Chemistry Letters, 13(13): 2167-2172 (2003).
International Search Report for PCT/US2008/010431 dated Oct. 13, 2009.

*Primary Examiner* — Emily Bernhardt
(74) *Attorney, Agent, or Firm* — Jeffrey A. Hagenah; Shelley Eberle

(57) ABSTRACT

The invention provides compounds of formula I:

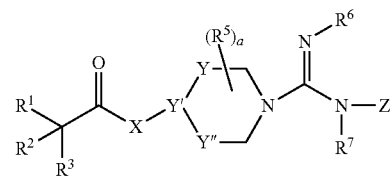

or a pharmaceutically acceptable salt thereof, wherein $R^{1-3}$, $R^{5-7}$, a, X, Y, Y', Y", and Z are as defined in the specification. These compounds are muscarinic receptor antagonists. The invention also provides pharmaceutical compositions containing such compounds, processes for preparing such compounds and methods of using such compounds to, for example, treat pulmonary disorders such as chronic obstructive pulmonary disease and asthma.

20 Claims, No Drawings

GUANIDINE-CONTAINING COMPOUNDS USEFUL AS MUSCARINIC RECEPTOR ANTAGONISTS

CROSS-REFERENCE TO RELATED APPLICATIONS

This application is a continuation application of U.S. Ser. No. 13/228,782, filed on Sep. 9, 2011, now allowed, which is a divisional application of U.S. Ser. No. 13/096,651, filed on Apr. 28, 2011 and issued as U.S. Pat. No. 8,039,489, which is a divisional application of U.S. Serial No. 12/231,861, filed on September 5, 2008, and issued as U.S. Pat. No. 7,960,385, which claims the benefit of U.S. Provisional Application No. 60/967,914, filed on Sep. 7, 2007; the disclosures of which are incorporated herein by reference in their entirety.

BACKGROUND OF THE INVENTION

1. Field of the Invention

The present invention relates to guanidine-containing compounds having muscarinic receptor antagonist or anticholinergic activity. The invention also relates to pharmaceutical compositions comprising these compounds, processes for preparing them and methods of use to treat pulmonary disorders.

2. State of the Art

Pulmonary or respiratory disorders, such as chronic obstructive pulmonary disease (COPD) and asthma, afflict many millions of people worldwide and such disorders are a leading cause of morbidity and mortality.

Muscarinic receptor antagonists are known to provide bronchoprotective effects and therefore, such compounds are useful for treating respiratory disorders, such as COPD and asthma. When used to treat such disorders, muscarinic receptor antagonists are typically administered by inhalation. However, even when administered by inhalation, a significant amount of the muscarinic receptor antagonist is often absorbed into the systemic circulation resulting in systemic side effects, such as dry mouth, mydriasis and cardiovascular side effects.

Additionally, many inhaled muscarinic receptor antagonists have a relatively short duration of action requiring that they be administered several times per day. Such a multiple-daily dosing regime is not only inconvenient but also creates a significant risk of inadequate treatment due to patient non-compliance with the required frequent dosing schedule.

Accordingly, a need exists for new muscarinic receptor antagonists. In particular, a need exists for muscarinic receptor antagonists having high potency, reduced systemic side effects when administered by inhalation, and a long duration of action thereby allowing for once-daily or even once-weekly dosing. In addition, a need exists for muscarinic receptor antagonists having high affinity for the receptor and a long receptor half life. Such compounds are expected to be particularly effective for treating pulmonary disorders, such as COPD and asthma, while reducing or eliminating side effects, such as dry-mouth and constipation.

SUMMARY OF THE INVENTION

The present invention provides novel guanidine-containing compounds which have muscarinic receptor antagonist or anticholinergic activity. Among other properties, compounds of this invention have been found to possess improved binding affinity for $hM_2$ and $hM_3$ muscarinic receptor subtypes, have longer receptor half-lives, have a larger therapeutic window, or have greater potency compared to related compounds. Accordingly, compounds of the invention are expected to be useful and advantageous as therapeutic agents for treating pulmonary disorders.

One aspect of the invention relates to compounds having formula I:

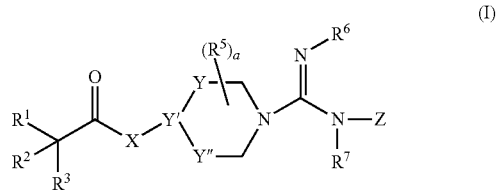

wherein:
$R^1$ is selected from —$C_{1-6}$alkyl, —$C_{2-6}$alkenyl, —$C_{3-9}$cycloalkyl, and heteroaryl; $R^2$ is selected from aryl and heteroaryl; $R^3$ is selected from H and —$C_{0-1}$alkylene-OH, or $R^3$ forms a double bond with $R^1$; or —$CR^1R^2R^3$ together form a group of formula:

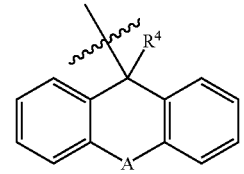

where A is selected from a bond, —O—, —S—, —$CH_2$—, —CH=CH—, —$CH_2CH_2$—, —NH—, and —N($CH_3$)—; and $R^4$ is selected from H, halo, —OH, —$C_{1-8}$alkyl, and —$C_{1-8}$alkoxy;

X is selected from a bond, —O—, and —O—$CH_2$—; when X is a bond, Y is —$CH_2$—, Y' is —N—, and Y" is —$CH_2$—; and when X is —O— or —O—$CH_2$—, Y' is —CH—, Y is a bond and Y" is —$CH_2$— or —$(CH_2)_2$—, or Y is —$CH_2$— and Y" is —$CH_2$—;

$R^5$ is selected from fluoro and —$C_{1-4}$alkyl; and a is 0 or an integer of from 1 to 3;

$R^6$ and $R^7$ are independently selected from H and —$C_{1-4}$alkyl, and further wherein one of $R^6$ or $R^7$ may be —$NH_2$;

Z is selected from H, —$C_{1-6}$alkyl, —$C_{1-3}$alkylene-Q, and —NH—$C_{0-1}$alkylene-Q; Q is selected from —$C_{3-7}$cycloalkyl, aryl, and heteroaryl; and Q is optionally substituted with 1-5 $R^8$ groups independently selected from halo, —$C_{1-4}$alkyl, —$C_{0-4}$alkylene-OH, cyano, —$C_{0-2}$alkylene-COOH, —C(O)O—$C_{1-4}$alkyl, —O—$C_{1-4}$alkyl, —S—$C_{1-4}$alkyl, —$CONR^{8a}R^{8b}$, —NH—C(O)—$C_{1-4}$alkyl, —N-di-$C_{1-4}$alkyl, and —$N^+(O)O$; $R^{8a}$ and $R^{8b}$ are independently selected from H and —$C_{1-4}$alkyl;

wherein $R^1$ and $R^2$ are optionally substituted with 1 to 5 $R^a$ groups independently selected from —$C_{1-4}$alkyl, —$C_{2-4}$alkenyl, —$C_{2-4}$alkynyl, —$C_{3-6}$cycloalkyl, cyano, halo, —$OR^b$, —$C(O)OR^b$, —$SR^b$, —$S(O)R^b$, —$S(O)_2R^b$, —$C(O)NR^cR^d$, and —$NR^cR^d$; each $R^b$ is independently selected from H, —$C_{1-4}$alkyl, —$C_{2-4}$alkenyl, —$C_{2-4}$alkynyl, and —$C_{3-6}$cycloalkyl; each $R^c$ and $R^d$ is independently selected from H, —$C_{1-4}$alkyl, —$C_{2-4}$alkenyl, —$C_{2-4}$alkynyl, and —$C_{3-6}$cycloalkyl;

wherein each alkyl, alkenyl, alkynyl, alkylene, and cycloalkyl group in $R^{a-d}$, $R^{4-8}$, and Z, is optionally substituted with 1 to 5 fluoro atoms; wherein each cycloalkyl in $R^{a-d}$ is optionally substituted with 1 to 3 substituents independently selected from —$C_{1-4}$alkyl, —$C_{2-4}$alkenyl, —$C_{2-4}$alkynyl, cyano, halo, —$O(C_{1-4}$alkyl), —$S(C_{1-4}$alkyl), —$S(O)(C_{1-4}$alkyl), —$S(O)_2(C_{1-4}$alkyl), —$NH_2$, —$NH(C_{1-4}$alkyl), and —$N(C_{1-4}$alkyl)$_2$, wherein each alkyl, alkenyl and alkynyl group is optionally substituted with 1 to 5 fluoro substituents; and the alkylene group in Z is optionally substituted with 1 or 2 substituents independently selected from —$C_{1-2}$alkyl and —OH; or a pharmaceutically acceptable salt thereof.

Among the compounds of formula I, compounds of particular interest are those having an inhibition dissociation constant ($K_i$) for binding to the $M_3$ receptor subtype of less than or equal to 100 nM; in particular having a $K_i$ less than or equal to 50 nM; more particularly having a $K_i$ less than or equal to 10 nM; and even more particularly having a $K_i$ less than or equal to 1.0 nM.

Another aspect of the invention relates to pharmaceutical compositions comprising a pharmaceutically acceptable carrier and a compound of the invention. Such compositions may optionally contain other therapeutic agents such as steroidal anti-inflammatory agents (e.g., corticosteroids), $\beta_2$ adrenergic receptor agonists, phosphodiesterase-4 inhibitors, and combinations thereof. Accordingly, in yet another aspect of the invention, a pharmaceutical composition comprises a compound of the invention, a second active agent, and a pharmaceutically acceptable carrier. Another aspect of the invention relates to a combination of active agents, comprising a compound of the invention and a second active agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of the invention and a first pharmaceutically acceptable carrier; and a second pharmaceutical composition comprising a second active agent and a second pharmaceutically acceptable carrier. This invention also relates to a kit containing such pharmaceutical compositions, for example where the first and second pharmaceutical compositions are separate pharmaceutical compositions.

Compounds of the invention possess muscarinic receptor antagonist activity, and are therefore expected to be useful as therapeutic agents for treating patients suffering from a disease or disorder that is treated by blocking the muscarinic receptor. Thus, one aspect of the invention relates to a method of producing bronchodilation in a patient, comprising administering to the patient a bronchodilation-producing amount of a compound of the invention. The invention is also directed to method of treating a pulmonary disorder such as chronic obstructive pulmonary disease or asthma, comprising administering to a patient a therapeutically effective amount of a compound of the invention. Another aspect of the invention relates to a method for antagonizing a muscarinic receptor in a mammal comprising administering to the mammal, a muscarinic receptor-antagonizing amount of a compound of the invention.

Since compounds of the invention possess muscarinic receptor antagonist activity, such compounds are also useful as research tools. Accordingly, one aspect of the invention relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a muscarinic receptor binding assay and a bronchoprotection assay in a mammal. Still another aspect of the invention relates to a method of studying a biological system or sample comprising a muscarinic receptor, the method comprising: (a) contacting the biological system or sample with a compound of the invention; and (b) determining the effects caused by the compound on the biological system or sample.

The invention is also directed to processes and intermediates useful for preparing compounds of the invention. Accordingly, another aspect of the invention relates to a process of preparing compounds of the invention, comprising: (a) coupling compound (1) and compound (2) under amide bond-forming conditions and deprotecting the product to form compound (3), or Mitsunobu coupling or transesterification of compound (1) and compound (4) and deprotecting the product to form compound (5); (b) reacting compound (3) or compound (5) with compound (6) to form compound (7); and (c) reacting compound (7) and compound (8) to provide a compound of formula I; wherein compounds (1) through (9) are as defined herein. In other aspects, the invention relates to products prepared by any of the processes described herein.

Yet another aspect of the invention relates to the use of a compound of the invention for the manufacture of a medicament, especially for the manufacture of a medicament useful for treating a pulmonary disorder or for antagonizing a muscarinic receptor in a mammal. Still another aspect of the invention relates to the use of a compound of the invention as a research tool. Other aspects and embodiments of the invention are disclosed herein.

DETAILED DESCRIPTION OF THE INVENTION

In one aspect, this invention relates to compounds having formula I:

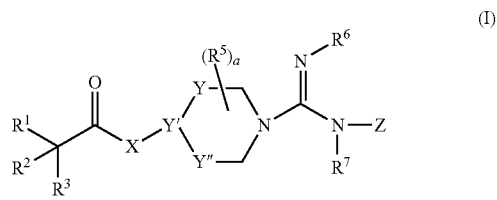

or a pharmaceutically acceptable salt thereof. This formula may also be depicted as:

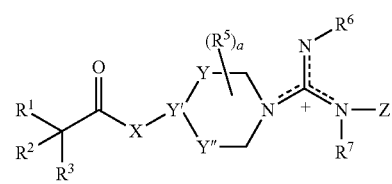

As used herein, the term "compound of the invention" includes all compounds encompassed by formula I such as the species embodied in formulas II-VIII. In addition, when the compound of the invention contain a basic or acidic group (e.g., amino or carboxyl groups), the compound can exist as a free base, free acid, or in various salt forms. All such salt forms are included within the scope of the invention. Accordingly, those skilled in the art will recognize that reference to a compound herein, for example, reference to a "compound of the invention" or a "compound of formula I" includes a compound of formula I as well as pharmaceutically acceptable salts of that compound unless otherwise indicated. Furthermore, solvates of compounds of formula I are included within the scope of the invention.

The compounds of the invention may contain one or more chiral centers and so may exist in a number of stereoisomeric forms. When such chiral centers are present, this invention relates to racemic mixtures, pure stereoisomers (i.e., enantiomers or diastereomers), stereoisomer-enriched mixtures, and the like unless otherwise indicated. When a chemical structure is depicted without any stereochemistry, it is understood that all possible stereoisomers are encompassed by such structure. Thus, for example, the term "compound of formula I" is intended to include all possible stereoisomers of the compound. Similarly, when a particular stereoisomer is shown or named herein, it will be understood by those skilled in the art that minor amounts of other stereoisomers may be present in the compositions of this invention unless otherwise indicated, provided that the utility of the composition as a whole is not eliminated by the presence of such other isomers. Individual enantiomers may be obtained by numerous methods that are well known in the art, including chiral chromatography using a suitable chiral stationary phase or support, or by chemically converting them into diastereomers, separating the diastereomers by conventional means such as chromatography or recrystallization, then regenerating the original enantiomers. Additionally, where applicable, all cis-trans or E/Z isomers (geometric isomers), tautomeric forms and topoisomeric forms of the compounds of this invention are included within the scope of this invention unless otherwise specified.

In particular, the compounds of formula I contain a chiral center at the carbon atom indicated by the symbol * in the following partial formula (shown without optional substituents for clarity), illustrated with the $R^1$ $C_{5-9}$cycloalkyl moiety being cyclopentyl, the $R^2$ aryl moiety being phenyl, and $R^3$ being —OH:

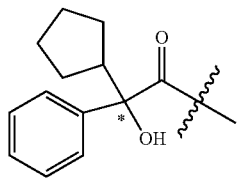

In one embodiment of this invention, the carbon atom identified by the symbol * has the (R) configuration. In this embodiment, compounds of formula I have the (R) configuration at the carbon atom identified by the symbol * or are enriched in a stereoisomeric form having the (R) configuration at this carbon atom. In another embodiment, the carbon atom identified by the symbol * has the (S) configuration. In this embodiment, compounds of formula I have the (S) configuration at the carbon atom identified by the symbol * or are enriched in a stereoisomeric form having the (S) configuration at this carbon atom.

The compounds of the invention, as well as those compounds used in their synthesis, may also include isotopically-labeled compounds, i.e., where one or more atoms have been enriched with atoms having an atomic mass different from the atomic mass predominately found in nature. Examples of isotopes that may be incorporated into the compounds of formula I, for example, include, but are not limited to, $^2H$, $^3H$, $^{13}C$, $^{14}C$, $^{15}N$, $^{18}O$ and $^{17}O$.

The compounds of the invention have been found to possess muscarinic receptor antagonist activity. Among other properties, compounds of the invention have been found to possess improved binding affinity for $hM_2$ and $hM_3$ muscarinic receptor subtypes, have longer receptor half-lives, and have greater potency compared to related compounds, and are expected to be useful as therapeutic agents for treating pulmonary disorders.

The nomenclature used herein to name the compounds of the invention is illustrated in the Examples herein. This nomenclature has been derived using the commercially-available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

$R^1$ may be a —$C_{1-6}$alkyl, —$C_{2-6}$alkenyl, —$C_{3-9}$cycloalkyl or heteroaryl group that is unsubstituted or substituted with 1 to 5 $R^a$ groups. $R^a$ is independently selected from —$C_{1-4}$alkyl, —$C_{2-4}$alkenyl, —$C_{2-4}$alkynyl, —$C_{3-6}$cycloalkyl, cyano, halo, —$OR^b$, —$C(O)OR^b$, —$SR^b$, —$S(O)R^b$, —$S(O)_2R^b$, —$C(O)NR^cR^d$, and —$NR^cR^d$. Each $R^b$ is independently selected from H, —$C_{1-4}$alkyl, —$C_{2-4}$alkenyl, —$C_{2-4}$alkynyl, and —$C_{3-6}$cycloalkyl. Each $R^c$ and $R^d$ group is independently selected from H, —$C_{1-4}$alkyl, —$C_{2-4}$alkenyl, —$C_{2-4}$alkynyl, and —$C_{3-6}$cycloalkyl. In one embodiment, $R^1$ is —$C_{3-9}$cycloalkyl; in another embodiment —$C_{3-6}$cycloalkyl, i.e., cyclopropyl, cyclobutyl, cyclopentyl or cyclohexyl; and in yet another embodiment $R^1$ is —$C_5$cycloalkyl, i.e., cyclopentyl. In one embodiment, $R^1$ is a —$C_{1-6}$alkyl group such as —$CH_2CH(CH_3)_2$. In another embodiment, $R^1$ is a —$C_{2-6}$alkenyl group such as —$CH_2CHCH_2$. In one embodiment, $R^1$ is unsubstituted. In another embodiment, $R^1$ is a heteroaryl, such as thiophenyl (including thiophen-2-yl and thiophen-3-yl).

Each alkyl, alkenyl, alkynyl, alkylene, and cycloalkyl group in $R^a$, $R^b$, $R^c$, and $R^d$, may be substituted with 1 to 5 fluoro atoms. In addition, each cycloalkyl in $R^{a-d}$ may be substituted with 1 to 3 substituents independently selected from —$C_{1-4}$alkyl, —$C_{2-4}$alkenyl, —$C_{2-4}$alkynyl, cyano, halo, —$O(C_{1-4}$alkyl), —$S(C_{1-4}$alkyl), —$S(O)(C_{1-4}$alkyl), —$S(O)_2(C_{1-4}$alkyl), —$NH_2$, —$NH(C_{1-4}$alkyl) and —$N(C_{1-4}$alkyl)$_2$, wherein each alkyl, alkenyl and alkynyl group is optionally substituted with 1 to 5 fluoro substituents.

$R^2$ may be an aryl group that is unsubstituted or substituted with 1 to 5 $R^a$ groups, which are defined above. In one embodiment, $R^2$ is phenyl. In another embodiment, $R^2$ is unsubstituted phenyl. In another embodiment, $R^2$ is a heteroaryl, such as thiophenyl (including thiophen-2-yl and thiophen-3-yl).

$R^3$ may be H or —$C_{0-1}$alkylene-OH, or may form a double bond with $R^1$, which can be depicted as:

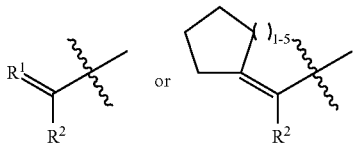

In one particular embodiment, $R^3$ is —OH. In addition, —$CR^1R^2R^3$ together may form a group of formula:

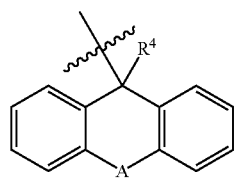

where A is a bond, —O—, —S—, —$CH_2$—, —CH=CH—, —$CH_2CH_2$—, —NH—, or —N($CH_3$)—, and $R^4$ is selected from H, halo, —OH, —$C_{1-8}$alkyl, and —$C_{1-8}$alkoxy. The alkyl group in $R^4$ may be substituted with 1 to 5 fluoro atoms. In one particular embodiment, —$CR^1R^2R^3$ together form:

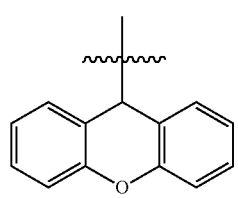

In this embodiment, A is —O— and $R^4$ is H, as shown.

In one embodiment, X is a bond, Y is —$CH_2$—, Y' is —N—, and Y" is —$CH_2$—, which can be depicted as:

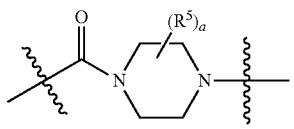

In another embodiment, when X is —O— or —O—$CH_2$—, Y' is —CH—, Y is a bond and Y" is —$CH_2$— or —$(CH_2)_2$—, which can be depicted as:

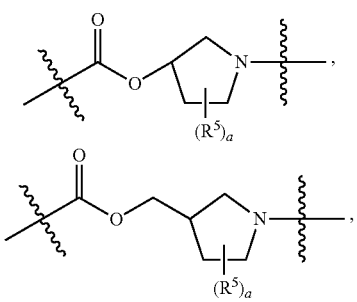

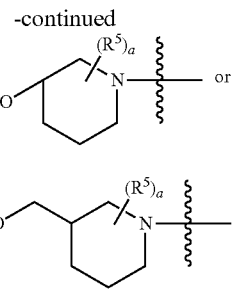

respectively. In another embodiment, when X is —O— or —O—$CH_2$—, Y' is —CH—, and both Y and Y" are —$CH_2$—, which can be depicted as:

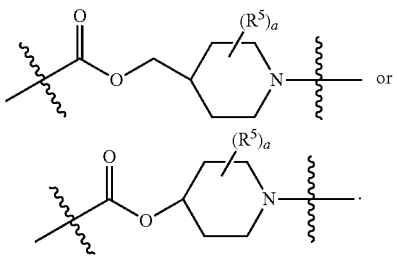

$R^5$ is selected from fluoro and —$C_{1-4}$alkyl. The value for a is 0 or an integer of from 1 to 3. In one particular embodiment, a is 0. The alkyl group in $R^5$ may be substituted with 1 to 5 fluoro atoms.

$R^6$ and $R^7$ are independently selected from H and —$C_{1-4}$alkyl. In addition, one of $R^6$ or $R^7$ may be —$NH_2$. In one particular embodiment, $R^6$ is hydrogen or —$C_{1-4}$alkyl. In another embodiment, $R^7$ is hydrogen. In yet another particular embodiment, both $R^6$ and $R^7$ are hydrogen. The alkyl group in $R^6$ and $R^7$ may be substituted with fluoro atoms. For example, $R^6$ and/or $R^7$ can be —$CH_3$ as well as —$CFH_2$, —$CF_2H$ or —$CF_3$.

Z is selected from hydrogen, —$C_{1-6}$alkyl, —$C_{1-3}$alkylene-Q, and —NH—$C_{0-1}$alkylene-Q. In one embodiment, Z is —$CH_2$-Q. In another embodiment, Z is —$(CH_2)_2$-Q. In still another embodiment, Z is —$(CH_2)_3$-Q. In still another embodiment, Z is —NH-Q. In yet another embodiment, Z is —NH—$CH_2$-Q. In another embodiment, Z is hydrogen or —$C_{1-6}$alkyl. Exemplary —$C_{1-6}$alkyl groups include methyl, propyl, butyl, and pentyl. The alkyl and alkylene groups in Z may be substituted with 1 to 5 fluoro atoms. Further, the alkylene group in Z may be substituted with 1 or 2 substituents independently selected from —$C_{1-2}$alkyl and —OH. For example, in one embodiment, Z is —CH($CH_3$)—.

Q is a —$C_{3-7}$cycloalkyl, aryl, or heteroaryl group. Exemplary —$C_{3-7}$cycloalkyl groups include cyclopropyl, cyclohexyl, and cycloheptyl. Exemplary aryl groups include phenyl and naphthyl. In one embodiment, Q is phenyl. Exemplary heteroaryl groups include pyrrolyl, imidazolyl, thiazolyl, oxazolyl, furanyl, thiophenyl, triazolyl, pyrazolyl, isoxazolyl, isothiazolyl, pyridinyl, pyrazinyl, pyridazinyl, pyrimidinyl, triazinyl, indolyl, benzofuranyl, benzopyranyl, benzothiophenyl, benzoimidazolyl, benzothiazolyl, benzodioxolyl, quinolyl, isoquinolyl, quinazolinyl, and quinoxalinyl groups. Of particular interest are thiazolyl (e.g., thiazol-2-yl and thiazol-4-yl), furanyl (e.g., furan-2-yl and furan-3-yl), thiophenyl (e.g., thiophen-2-yl and thiophen-3-yl), pyrazolyl (e.g., 1H-pyrazol-3-yl), pyridinyl (e.g., pyridin-2-yl), indolyl (e.g., 1H-indol-2-yl, 1H-indol-4-yl and 1H-indol-5-yl), benzofuranyl (e.g., benzofuran-5-yl), benzothiophenyl (e.g., benzo[b]thiophen-2-yl and benzo[b]thiophen-5-yl), and benzodioxolyl (e.g., benzo[1,3]dioxol-5-yl) groups.

Q may be substituted with 1 to 5 $R^8$ groups independently selected from halo (e.g., Cl and F), —$C_{1-4}$alkyl (e.g., —$CH_3$), —$C_{0-4}$alkylene-OH (e.g., —OH and —$CH_2OH$), cyano, —$C_{0-2}$alkylene-COOH, —C(O)O—$C_{1-4}$alkyl (e.g., —C(O)O—$CH_3$), —O—$C_{1-4}$alkyl (e.g., —$OCH_3$), —S—$C_{1-4}$alkyl (e.g., —S—$CH_3$), —$CONR^{8a}R^{8b}$, —NH—C(O)—$C_{1-4}$alkyl, —N-di-$C_{1-4}$alkyl, and —$N^+(O)O$, where $R^{8a}$ and $R^{8b}$ are independently selected from H and —$C_{1-4}$alkyl. Each alkyl and alkylene group in $R^8$ may be substituted with 1 to 5 fluoro atoms. For example, $R^8$ can be a fluoro substituted —$C_{1-4}$alkyl group such as —$CF_3$ or a fluoro substituted —O—$C_{1-4}$alkyl group such as —$OCF_3$.

In one embodiment, Q is substituted with one $R^8$ group selected from halo, —$C_{1-4}$alkyl, —$C_{0-4}$alkylene-OH, cyano, —C(O)O—$C_{1-4}$alkyl, —O—$C_{1-4}$alkyl, —S—$C_{1-4}$alkyl, and —$CONR^{8a}R^{8b}$, where each alkyl group is optionally substituted with 1 to 3 fluoro atoms. In another embodiment, Q is substituted with two $R^8$ groups that are halo groups (which may be the same or different). In one embodiment, Q is an unsubstituted —$C_{3-7}$cycloalkyl group. In one embodiment, Q is an unsubstituted aryl group. In another embodiment, Q is an aryl group having one $R^8$ group selected from halo, —$C_{1-4}$alkyl, cyano, —$C_{0-2}$alkylene-COOH, —C(O)O—$C_{1-4}$alkyl, —O—$C_{1-4}$alkyl, —S—$C_{1-4}$alkyl, —$CONR^{8a}R^{8b}$, where each alkyl group is optionally substituted with 1 to 3 fluoro atoms. In yet another embodiment, Q is an aryl group having two $R^8$ groups that are halo groups. In one embodiment, Q is an unsubstituted heteroaryl group. In another embodiment, Q is a heteroaryl group having one $R^8$ group that is a —$C_{1-4}$alkyl group.

In one embodiment, the invention relates to compounds having formula I, where $R^1$ is isobutyl, cyclopentyl, or thiophenyl; $R^2$ is phenyl or thiophenyl; $R^3$ is —OH; or —$CR^1R^2R^3$ together form a group of formula:

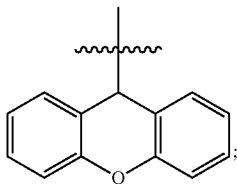

a is 0; $R^6$ is H or —$C_{1-4}$alkyl; $R^7$ is H; Z is H, —$C_{1-6}$alkyl, —$C_{1-3}$alkylene-Q, or —NH—$C_{0-1}$alkylene-Q; Q is cyclohexyl, cycloheptyl, phenyl, benzodioxolyl, benzofuranyl, benzothiophenyl, furanyl, indolyl, pyrazolyl, pyridinyl, thiazolyl, or thiophenyl; Q is optionally substituted with 1-2 $R^8$ groups independently selected from halo, —$C_{1-4}$alkyl, —$C_{0-4}$alkylene-OH, cyano, —C(O)O—$C_{1-4}$alkyl, —O—$C_{1-4}$alkyl, —S—$C_{1-4}$alkyl, and —$CONH_2$; and the alkyl groups in $R^8$ are optionally substituted with 1 to 5 fluoro atoms.

In another embodiment, the invention relates to a compound having formula II:

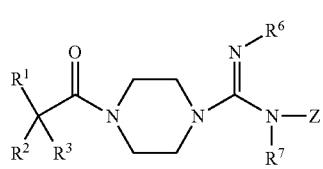

(II)

or a pharmaceutically acceptable salt thereof, where $R^{1-3}$, $R^{6-7}$, and Z are as defined for formula I. In one particular embodiment, the invention relates to compounds of formula II, where: $R^1$ is cyclopentyl or thiophenyl; $R^2$ is phenyl or thiophenyl; $R^3$ is —OH; $R^6$ is H or —$C_{1-2}$alkyl; $R^7$ is H; Z is —$C_{1-6}$alkyl, —$C_{1-3}$alkylene-Q, or —NH—$C_{0-1}$alkylene-Q; Q is cyclohexyl, cycloheptyl, phenyl, benzodioxolyl, benzofuranyl, benzothiophenyl, furanyl, indolyl, pyrazolyl, pyridinyl, thiazolyl, or thiophenyl; Q is optionally substituted with 1-2 $R^8$ groups independently selected from halo, —$C_{1-4}$alkyl, —$C_{0-4}$alkylene-OH, cyano, —C(O)O—$C_{1-4}$alkyl, —O—$C_{1-4}$alkyl, —S—$C_{1-4}$alkyl, and —$CONH_2$; and the alkyl groups in $R^8$ are optionally substituted with 1 to 5 fluoro atoms.

Yet another aspect of the invention relates to compounds having formula IIa:

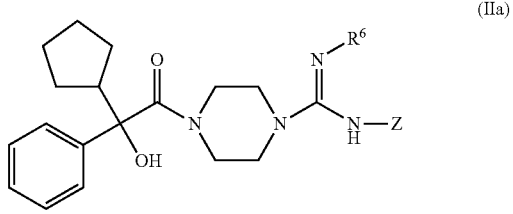

(IIa)

or a pharmaceutically acceptable salt thereof, where $R^6$ and Z are as defined for formula I. In one particular embodiment, the invention relates to compounds of formula IIa, where: $R^6$ is H or —$C_{1-2}$alkyl; Z is —$C_{1-6}$alkyl, —$C_{1-3}$alkylene-Q, or —NH—$C_{0-1}$alkylene-Q; Q is cyclohexyl, cycloheptyl, phenyl, benzodioxolyl, benzofuranyl, benzothiophenyl, furanyl, indolyl, pyrazolyl, pyridinyl, thiazolyl, or thiophenyl; Q is optionally substituted with 1-2 $R^8$ groups independently selected from halo, —$C_{1-4}$alkyl, —$C_{0-4}$alkylene-OH, cyano, —C(O)O—$C_{1-4}$alkyl, —O—$C_{1-4}$alkyl, —S—$C_{1-4}$alkyl, and —$CONH_2$; and the alkyl groups in $R^8$ are optionally substituted with 1 to 5 fluoro atoms.

Still another aspect of the invention relates to compounds having formula IIb:

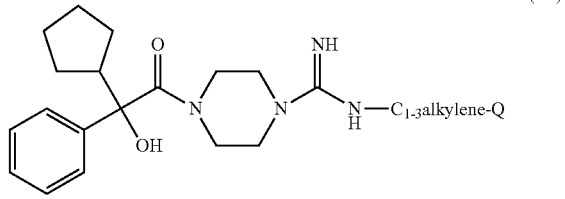

(IIb)

or a pharmaceutically acceptable salt thereof, where Q is as defined for formula I. In one particular embodiment, the invention relates to compounds of formula IIb, where: Q is cyclohexyl, cycloheptyl, phenyl, benzodioxolyl, benzofuranyl, benzothiophenyl, furanyl, indolyl, pyrazolyl, pyridinyl, thiazolyl, or thiophenyl; Q is optionally substituted with 1-2 $R^8$ groups independently selected from halo, —$C_{1-4}$alkyl, —$C_{0-4}$alkylene-OH, cyano, —C(O)O—$C_{1-4}$alkyl, —O—$C_{1-4}$alkyl, —S—$C_{1-4}$alkyl, and —$CONH_2$; and the alkyl groups in $R^8$ are optionally substituted with 1 to 5 fluoro atoms. In another embodiment, the invention relates to compounds of formula IIb, where Q is furanyl or thiophenyl.

Still another aspect of the invention relates to compounds having formula IIc:

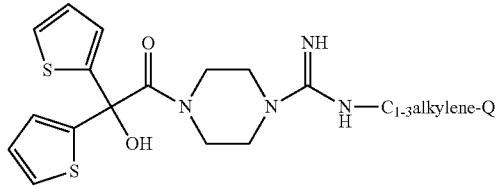
(IIc)

or a pharmaceutically acceptable salt thereof, where Z is as defined for formula I. In one particular embodiment, the invention relates to compounds of formula IIc, where: Q is phenyl, furanyl, or thiophenyl; and the phenyl in Q is optionally substituted with 1-2 $R^8$ groups independently selected from halo and —$C_{0-4}$alkylene-OH.

In yet another embodiment, the invention relates to a compound having formula III:

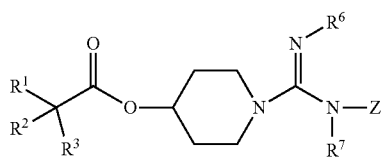
(III)

or a pharmaceutically acceptable salt thereof, where $R^{1-3}$, $R^{6-7}$, and Z are as defined for formula I. In one particular embodiment, the invention relates to compounds of formula III where: $R^1$ is cyclopentyl; $R^2$ is phenyl; $R^3$ is —OH; $R^6$ and $R^7$ are H; Z is —$C_{1-3}$alkylene-Q; Q is phenyl, benzofuranyl, furanyl, pyridinyl, or thiophenyl; and the phenyl in Q is optionally substituted with 1-2 $R^8$ groups independently selected from halo and —$C_{0-4}$alkylene-OH.

In still another embodiment, the invention relates to a compound having formula IV:

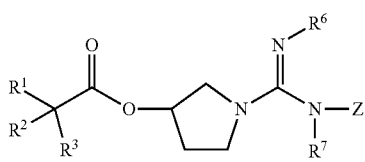
(IV)

or a pharmaceutically acceptable salt thereof, where $R^{1-3}$, $R^{6-7}$, and Z are as defined for formula I. In one particular embodiment, the invention relates to compounds of formula IV where: $R^1$ is isobutyl or cyclopentyl; $R^2$ is phenyl; $R^3$ is —OH; $R^6$ and $R^7$ are H; Z is —$C_{1-6}$alkyl or —$C_{1-3}$alkylene-Q; Q is phenyl, furanyl, pyridinyl, or thiophenyl; Q is optionally substituted with 1-2 $R^8$ groups independently selected from halo, —$C_{1-4}$alkyl, —$C_{0-4}$alkylene-OH, and —O—$C_{1-4}$alkyl; and the alkyl groups in $R^8$ are optionally substituted with 1 to 5 fluoro atoms.

A particular group of compounds of formula I are those disclosed in U.S. Provisional Application No. 60/967,914, filed on Sep. 7, 2007. This group includes compounds of formula (I'):

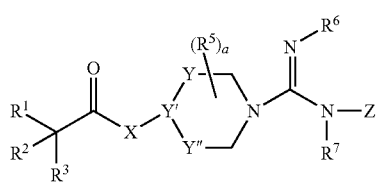
(I)

wherein: $R^1$ is selected from —$C_{1-6}$alkyl, —$C_{2-6}$alkenyl, and —$C_{3-9}$cycloalkyl; $R^2$ is aryl; $R^3$ is selected from H and —$C_{0-1}$alkylene-OH; or forms a double bond with $R^1$; or —$CR^1R^2R^3$ together form a group of formula:

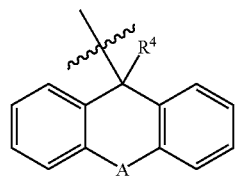

where A is a bond, —O—, —S—, —$CH_2$—, —CH═CH—, —$CH_2CH_2$—, —NH—, or —N($CH_3$)—; and where $R^4$ is selected from H, halo, —OH, —$C_{1-8}$alkyl, and —$C_{1-8}$alkoxy; X is a bond, —O— or —O—$CH_2$—; when X is a bond, Y is —$CH_2$—, Y' is —N—, and Y" is —$CH_2$—; when X is —O— or —O—$CH_2$—, Y' is —CH—, and Y is a bond and Y" is —$CH_2$— or —($CH_2$)$_2$—, or Y is —$CH_2$— and Y" is —$CH_2$—; $R^5$ is selected from fluoro and —$C_{1-4}$alkyl; and a is 0 or an integer of from 1 to 3; $R^6$ and $R^7$ are independently selected from H and —$C_{1-4}$alkyl, and further wherein one of $R^6$ or $R^7$ may be —$NH_2$; Z is selected from H, —$C_{1-6}$alkyl, —$C_{1-3}$alkylene-Q, and —NH—$C_{0-1}$alkylene-Q, where Q is selected from —$C_{3-7}$cycloalkyl, aryl, or heteroaryl, optionally substituted with 1-5 $R^8$ groups independently selected from halo, —$C_{1-4}$alkyl, —$C_{0-4}$alkylene-OH, cyano, —$C_{0-2}$alkylene-COOH, —C(O)O—$C_{1-4}$alkyl, —O—$C_{1-4}$alkyl, —S—$C_{1-4}$alkyl, —CONR$^{8a}$R$^{8b}$, —NH—C(O)—$C_{1-4}$alkyl, —N-di-$C_{1-4}$alkyl, and —N$^+$(O)O, where $R^{8a}$ and $R^{8b}$ are independently selected from H and —$C_{1-4}$alkyl; wherein $R^1$ and $R^2$ are optionally substituted with 1 to 5 $R^a$ groups selected from —$C_{1-4}$alkyl, —$C_{2-4}$alkenyl, —$C_{2-4}$alkynyl, —$C_{3-6}$cycloalkyl, cyano, halo, —OR$^b$, —C(O)OR$^b$, —SR$^b$, —S(O)R$^b$, —S(O)$_2$R$^b$, —C(O)NR$^c$R$^d$ and —NR$^c$R$^d$; where each $R^b$ is independently selected from H, —$C_{1-4}$alkyl, —$C_{2-4}$alkenyl, —$C_{2-4}$alkynyl, and —$C_{3-6}$cycloalkyl; and each $R^c$ and $R^d$ is independently selected from H, —$C_{1-4}$alkyl, —$C_{2-4}$alkenyl, —$C_{2-4}$alkynyl, and —$C_{3-6}$cycloalkyl; wherein each alkyl, alkenyl, alkynyl, alkylene, and cycloalkyl group in $R^{a-d}$, $R^{4-8}$, and Z, is optionally substituted with 1 to 5 fluoro atoms; wherein each cycloalkyl in $R^{a-d}$ is optionally substituted with 1 to 3 substituents independently selected from —$C_{1-4}$alkyl, —$C_{2-4}$alkenyl, —$C_{2-4}$alkynyl, cyano, halo, —O($C_{1-4}$alkyl), —S($C_{1-4}$alkyl), —S(O)($C_{1-4}$alkyl), —S(O)$_2$($C_{1-4}$alkyl), —$NH_2$, —NH($C_{1-4}$alkyl) and —N($C_{1-4}$alkyl)$_2$, wherein each alkyl, alkenyl and alkynyl group is optionally substituted with 1 to 5 fluoro substituents; and the alkylene group in Z is optionally substituted with 1 or 2 substituents independently selected from —$C_{1-2}$alkyl and —OH; or a pharmaceutically acceptable salt thereof.

In addition, particular compounds of the invention that are of interest include those set forth in the Examples below, as well as the pharmaceutically acceptable salts thereof.

Definitions

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example —$C_{1-2}$alkyl, —$C_{1-4}$alkyl, and —$C_{1-6}$alkyl. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—$C_{1-4}$alkyl" means an alkyl group having from 1 to 4 carbon atoms, and the term "—$C_{5-9}$cycloalkyl" means a cycloalkyl group having from 5 to 9 carbon atoms, where the carbon atoms are in any acceptable configuration.

The term "alkylene" means a divalent saturated hydrocarbon group that may be linear or branched. Unless otherwise defined, such alkylene groups typically contain from 0 to 10 carbon atoms and include, for example, —$C_{0-1}$alkylene-, —$C_{0-2}$alkylene-, —$C_{0-4}$alkylene-, —$C_{0-5}$alkylene-, —$C_{1-4}$alkylene-, —$C_{1-2}$alkylene-, —$C_{2-4}$alkylene-, —$C_{2-5}$alkylene-, and —$C_{3-6}$alkylene-. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term includes zero carbons such as —$C_{0-1}$alkylene- or —$C_{0-5}$alkylene-, such terms are intended to include the absence of carbon atoms, that is, the alkylene group is not present except for a covalent bond attaching the groups separated by the alkylene term.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms and include, for example, —$C_{2-4}$alkenyl and —$C_{2-6}$alkenyl. Representative alkenyl groups include, by way of example, ethenyl, n-propenyl, isopropenyl, n-but-2-enyl, n-hex-3-enyl and the like. The term "alkenylene" means a divalent alkenyl group, and exemplary alkenylene groups include —$C_{2-3}$alkenylene-.

The term "alkoxy" means a monovalent group of the formula —O-alkyl, where alkyl is as defined herein. Unless otherwise defined, such alkylene groups typically contain from 1 to 10 carbon atoms and include, for example, —$C_{1-4}$alkoxy and —$C_{1-8}$alkoxy. Representative alkoxy groups include, by way of example, methoxy, ethoxy, n-propoxy, isopropoxy, n-butoxy, sec-butoxy, isobutoxy, tert-butoxy and the like.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms and include, for example, —$C_{2-4}$alkynyl and —$C_{2-6}$alkynyl. Representative alkynyl groups include, by way of example, ethynyl, n-propynyl, n-but-2-ynyl, n-hex-3-ynyl and the like.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms and include, for example, —$C_{6-10}$aryl. Representative aryl groups include, by way of example, phenyl and naphthalene-1-yl, naphthalene-2-yl, and the like.

The term "cycloalkyl" means a monovalent saturated carbocyclic hydrocarbon group. Unless otherwise defined, such cycloalkyl groups typically contain from 3 to 10 carbon atoms and include, for example, —$C_{3-6}$cycloalkyl, —$C_{3-7}$cycloalkyl, and —$C_{5-9}$cycloalkyl. Representative cycloalkyl groups include, by way of example, cyclopropyl, cyclobutyl, cyclopentyl, cyclohexyl and the like.

The term "divalent hydrocarbon group" means a divalent hydrocarbon group which is composed primarily of carbon and hydrogen atoms and which optionally contains one or more heteroatoms. Such divalent hydrocarbon groups may be branched or unbranched, saturated or unsaturated, acyclic or cyclic, aliphatic or aromatic, or combinations thereof. The divalent hydrocarbon group can optionally contain heteroatoms incorporated into the hydrocarbon chain or as substituents attached to the hydrocarbon chain.

The term "halo" means fluoro, chloro, bromo and iodo.

As used herein, the phrase "having the formula" or "having the structure" is not intended to be limiting and is used in the same way that the term "comprising" is commonly used.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms and include, for example, —$C_{2-9}$heteroaryl. Representative heteroaryl groups include, by way of example, pyrrolyl, imidazolyl, thiazolyl, oxazolyl, furanyl, thiophenyl, triazolyl, pyrazolyl, isoxazolyl, isothiazolyl, pyridinyl, pyrazinyl, pyridazinyl, pyrimidinyl, triazinyl, indolyl, benzofuranyl, benzopyranyl, benzothiophenyl, benzoimidazolyl, benzothiazolyl, benzodioxolyl, quinolyl, isoquinolyl, quinazolinyl, quinoxalinyl and the like, where the point of attachment is at any available carbon or nitrogen ring atom.

The term "optionally substituted" means that group in question may be unsubstituted or it may be substituted one or several times, such as 1 to 3 times or 1 to 5 times. For example, an alkyl group that is "optionally substituted" with 1 to 5 fluoro atoms, may be unsubstituted, or it may contain 1, 2, 3, 4, or 5 fluoro atoms.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable with other components of the composition. Such pharmaceutically acceptable materials typically have met the required standards of toxicological and manufacturing testing, and include those materials identified as suitable inactive ingredients by the U.S. Food and Drug Administration.

The term "pharmaceutically acceptable salt" means a salt prepared from a base or an acid which is acceptable for administration to a patient, such as a mammal (e.g., salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety and an acidic moiety, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxy-naphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" means an amount sufficient to effect treatment when administered to a patient in need of treatment, i.e., the amount of drug needed to obtain the desired therapeutic effect. For example, a therapeutically effective amount for treating chronic obstructive pulmonary disease (COPD) is an amount of compound needed to, for example, reduce, suppress, eliminate or prevent, the symptoms of (COPD), or to treat the underlying cause of (COPD). On the other hand, an "effective" amount is that amount needed to obtain a desired result, which may not necessarily be a therapeutically effective amount. For example, when studying a system comprising for antagonizing a muscarinic receptor, an "effective amount" may be the amount needed to antagonize the receptor.

The term "treating" or "treatment" as used herein means the treating or treatment of a disease or medical condition (such as COPD) in a patient, such as a mammal (particularly a human) that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating COPD" would include preventing COPD from occurring, ameliorating COPD, suppressing COPD, and alleviating the symptoms of COPD. The term "patient" is intended to include those animals, such as humans, that are in need of treatment or disease prevention, that are presently being treated for disease prevention or treatment of a specific disease or medical condition, as well as test subjects in which compounds of the invention are being evaluated or being used in a assay, for example an animal model.

All other terms used herein are intended to have their ordinary meaning as understood by those of ordinary skill in the art to which they pertain.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (i.e., reaction temperatures, times, mole ratios of reactants, solvents, pressures, etc.) are given, other process conditions can also be used unless otherwise stated. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Functional groups that may be protected so as to prevent undesired reactions include, by way of example, carboxy groups, amino groups, hydroxyl groups, thiol groups, carbonyl groups and the like. Representative carboxy-protecting groups include, but are not limited to, esters, such as methyl, ethyl, t-butyl, benzyl (Bn), p-methoxybenzyl (PMB), 9-fluoroenylmethyl (Fm), trimethylsilyl (TMS), t-butyldimethylsilyl (TBS), diphenylmethyl (benzhydryl, DPM) and the like; amides and hydrazides. Representative hydroxyl-protecting groups include, but are not limited to, silyl groups including triC$_{1-6}$alkylsilyl groups, such as trimethylsilyl (TMS), triethylsilyl (TES), tert-butyldimethylsilyl (TBS) and the like; esters (acyl groups) including C$_{1-6}$alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like; and ethers. Representative protecting groups for thiol groups include thioethers and thioesters. Representative protecting groups for carbonyl groups include acetals and ketals. Protecting groups other than those described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein. More specifically, the following abbreviations and reagents are used in the schemes presented below:

P represents an "amino-protecting group," a term that is used herein to mean a protecting group suitable for preventing undesired reactions at an amino group. Representative amino-protecting groups include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Standard deprotection techniques are used to remove the $P^1$ group. For example, deprotection of the N—BOC group can use a reagent such as HCl or 4M HCl in 1,4-dioxane.

Suitable bases for use in these schemes include, by way of illustration and not limitation, potassium carbonate, calcium carbonate, sodium carbonate, triethylamine, pyridine, 1,8-diazabicyclo-[5.4.0]undec-7-ene (DBU), N,N-diisopropylethylamine (DIPEA), sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), toluene, N,N-dimethylformamide (DMF), dimethyl sulfoxide (DMSO), dichloromethane (DCM), chloroform, carbon tetrachloride ($CHCl_3$), 1,4-dioxane, methanol, ethanol, water, and the like.

Suitable carboxylic acid/amine coupling reagents include 1-hydroxybenzotriazole hydrate (HOBt), benzotriazol-1-yloxytris(dimethylamino)phosphonium hexafluorophosphate (PyBOP), O-(7-azabenzotriazol-1-yl-N,N,N',N' tetramethyluronium hexafluorophosphate (HATU), dicyclohexylcarbodiimide (DCC), N-(3-dimethylaminopropyl)-N'-ethylcarbodiimide (EDCI), carbonyldiimidazole (CDI), and the like. Coupling reactions are conducted in an inert diluent in the presence of a base, and are performed under conventional amide bond-forming conditions.

All reactions are typically conducted at a temperature within the range of about −78° C. to 100° C., for example at room temperature. Typically, reactions are monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the mixture may be further treated in order to obtain the desired product. For example, the mixture may be subjected to one or more of the following procedures: stripping or partitioning (e.g., between ethyl acetate and water or between 5% THF in ethyl acetate and 1M phosphoric acid); extraction (e.g., with ethyl acetate, $CHCl_3$, DCM, KOH/chloroform); washing (e.g., with saturated aqueous NaCl, saturated $NaHCO_3$, $Na_2CO_3$ (5%), $CHCl_3$, HCl or NaOH); drying (e.g., over $MgSO_4$ or $NaSO_4$); solvent removal (e.g., in vacuo); filtering; being concentrated (e.g., in vacuo); and/or purification (e.g., silica gel chromatography, flash chromatography, or reverse phase-HPLC).

By way of illustration, compounds of formula I can be prepared by one or more of the following exemplary processes. The reactants are all commercially available and/or can be readily synthesized by techniques that are well known in the art.

Formation of the Head Group where X is a Bond

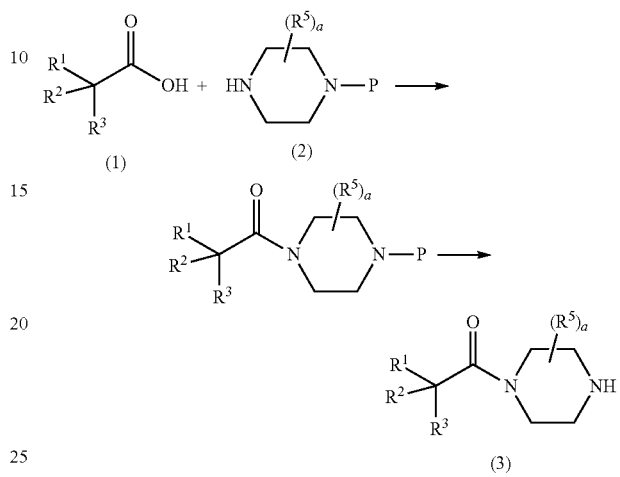

Compound (3) is formed by coupling compounds (1) and (2) under conventional amide bond-forming conditions, followed by a deprotection step.

Examples of compound (1) include (R)-cyclopentylhydroxyphenyl acetic acid ($R^1$ is cyclopentyl, $R^2$ is phenyl and $R^3$ is hydroxy). Examples of compound (2) include t-butyl 1-piperazinecarboxylate (a is 0, $P^1$ is BOC).

Formation of the Head Group where X is —O—

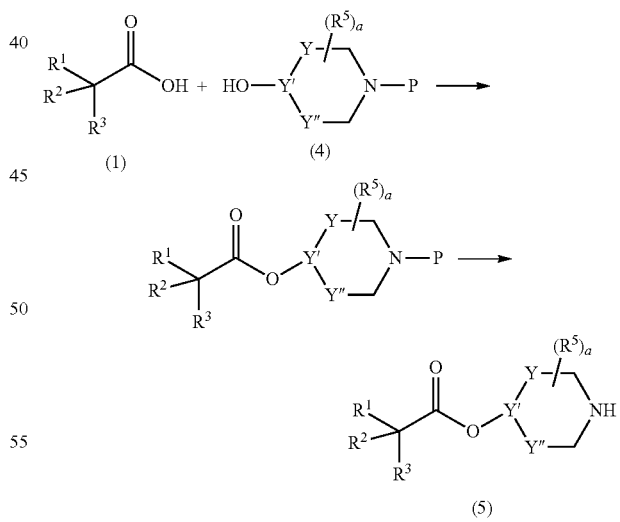

Compound (5) is formed by a Mitsunobu coupling reaction (Mitsunobu and Yamada (1967) *M. Bull. Chem. Soc. JPN.* 40:2380-2382). Compound (1) and compound (4) are reacted in the presence of a phosphine catalyst such as triphenylphosphine and an azodicarboxylate such as diethyl azodicarboxylate or diisopropyl azodicarboxylate, followed by a deprotection step to yield compound (5). Compound (5) can also be prepared by transesterification.

Examples of compound (1) include (R)-cyclopentylhydroxyphenyl acetic acid ($R^1$ is cyclopentyl, $R^2$ is phenyl and $R^3$ is hydroxy). Examples of compound (4) include (R)-3-hydroxypyrrolidine-1-carboxylic acid t-butyl ester (a is 0, $P^1$ is BOC, Y is a bond, Y' is —CH— and Y" is —$CH_2$—), 4-hydroxypiperidine-1-carboxylic acid t-butyl ester (a is 0, $P^1$ is BOC, Y is —$CH_2$—, Y' is —CH—, and Y" is —$CH_2$—) or (R)-3-hydroxypiperidine-1-carboxylic acid t-butyl ester (a is 0, $P^1$ is BOC, Y is a bond, Y' is —CH— and Y" is —$(CH_2)_2$—.

Addition of the Guanidine Moiety to the Head Group

Displacement of $1^{st}$ Benzotriazole Moiety

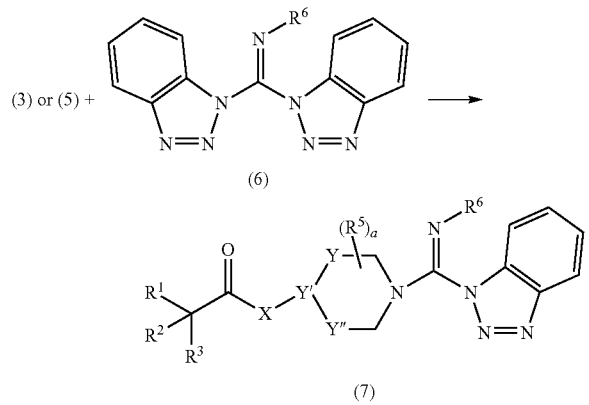

DIPEA is added to compound (3) or compound (5) in an appropriate solvent. Compound (6), the guanidinylating agent, is then added and the reaction stirred at room temperature until completion, typically from 30 minutes to several hours, to yield compound (7), which is used directly in the next step. Compound (6) is readily prepared by the method described in Katritzky et al. (2000) *J. Org. Chem.* 65(23): 8080-8082. An example of compound (6) is C-(bis-benzotriazol-1-yl)methylene amine ($R^6$ is H).

Substituted Guanidine Formation

Formation of Tri- or Tetra-substituted Guanidine

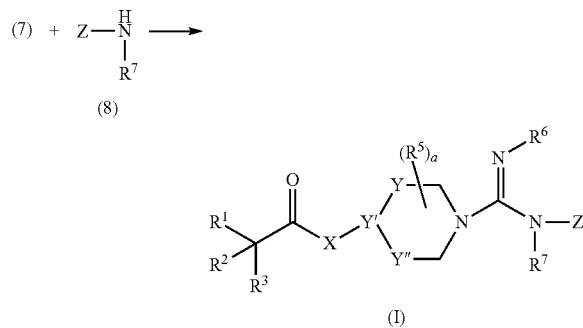

Compound (7) is added to compound (8) and the mixture is maintained at room temperature or heated (~60° C.) until completion, typically about 14-24 hours. The reaction is then cooled to room temperature, if needed, and the solvent removed. The crude material is then purified to afford a compound of formula I. Examples of compound (8) include 2-thiophenemethyl amine, 4-hydroxybenzyl amine, and benzylamine.

Further details regarding specific reaction conditions and other procedures for preparing representative compounds of the invention or intermediates thereof are described in the Examples set forth below.

Utility

Compounds of the invention possess muscarinic receptor antagonist activity, and in one embodiment, at nanomolar potencies. In one embodiment, compounds of the invention are selective for inhibition of $M_3$ muscarinic receptor subtype activity over $M_2$ muscarinic receptor subtype activity. In another embodiment, compounds of the invention are selective for inhibition of $M_3$ and $M_2$ muscarinic receptor subtype activity over $M_1$, $M_4$, and $M_5$ muscarinic receptor subtype activity. Additionally, compounds of the invention are expected to possess a desirable duration of action. Accordingly, in another specific embodiment, the invention relates to compounds having a duration of action greater than about 24 hours. Moreover, compounds of the invention are also expected to possess reduced side effects, such as dry mouth, at efficacious doses when administered by inhalation compared to other known muscarinic receptor antagonists administered by inhalation (such as tiotropium).

One measure of the affinity of a compound for the $M_3$ receptor subtype is the inhibition dissociation constant ($K_i$) for binding to the receptor. Compounds of the invention are expected to have a $K_i$ for the $M_3$ receptor subtype of less than or equal to 100 nM, as determined, for example, by an in vitro radioligand displacement assay. Compounds of particular interest include those having a $K_i$ less than or equal to 50 nM, and in another embodiment, the compounds have a $K_i$ less than or equal to 10 nM, and in yet another embodiment, the compounds have a $K_i$ less than or equal to 1.0 nM. Compounds of even more particular interest include those having a $K_i$ less than or equal to 500 pM, and in another embodiment, the compounds have a $K_i$ less than or equal to 200 pM. It is noted that in some cases, compounds of the invention may possess weak muscarinic receptor antagonist activity. In such cases, those of skill in the art will recognize that these compounds still have utility as research tools.

Also of particular interest are those compounds having an $ID_{50}$ of less than or equal to 100 µg/mL at 24 hours post dosing, more particularly those compounds having an $ID_{50}$ of less than or equal to 30 µg/mL at 24 hours post dosing.

Exemplary assays to determine properties of compounds of the invention, such as the muscarinic receptor antagonizing activity, are described in the Examples and include by way of illustration and not limitation, assays that measure $hM_1$, $hM_2$, $hM_3$, $hM_4$, and $hM_5$ muscarinic receptor binding (for example, as described in Assay 1). Useful functional assays to determine the muscarinic receptor antagonizing activity of compounds of the invention include by way of illustration and not limitation, assays that measure ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(γ-thio)triphosphate ([$^{35}$S]GTPγS) into isolated membranes via receptor catalyzed exchange of [$^{35}$S]GTPγS for GDP, ligand-mediated changes in free intracellular calcium ions (measured, for example, with a fluorescence-linked imaging plate reader or FLIPR® from Molecular Devices, Inc.), and the like. Exemplary assays are described in Assay 2. Compounds of this invention are expected to antagonize or decrease the activation of muscarinic receptors in any of the assays listed above, or assays of a similar nature, and will typically be used in these studies at a concentration ranging from about 0.1-100 nanomolar. Thus, the aforementioned assays are useful in determining the therapeutic utility, for example, the bronchodilating activity, of compounds of the invention.

Other properties and utilities of compounds of the invention can be demonstrated using various in vitro and in vivo assays well-known to those skilled in the art. For example, the in vivo potency of compounds of the invention can be measured in an animal model such as the Einthoven model. Briefly, the bronchodilator activity of a compound is evaluated in an anesthetized animal (the Einthoven model), which uses ventilation pressure as a surrogate measure of airway resistance. See, for example, Einthoven (1892) *Pfugers Arch.* 51:367-445; and Mohammed et al. (2000) *Pulm Pharmacol Ther.*13(6):287-92, as well as Assay 3 which describes a rat Einthoven model. In one embodiment, a compound of the invention administered at a dose of 100 µg/ml in the rat Einthoven model exhibits greater than or equal to 35% inhibition of the bronchoconstrictor response at 24 hours, and in another embodiment exhibits greater than or equal to 70% inhibition at 24 hours. Another useful in vivo assay is the rat antisialagogue assay (for example, as described in Assay 4).

Compounds of the invention are expected to be useful as therapeutic agents for treating medical conditions mediated by muscarinic receptors. Thus it is expected that patients suffering from a disease or disorder that is treated by blocking the muscarinic receptor can be treated by administering a therapeutically effective amount of a muscarinic receptor antagonist of the invention. Such medical conditions include, by way of example, pulmonary disorders or diseases including those associated with reversible airway obstruction, such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders, such as overactive bladder or detrusor hyperactivity and their symptoms; gastrointestinal tract disorders, such as irritable bowel syndrome, diverticular disease, achalasia, gastrointestinal hypermotility disorders and diarrhea; cardiac arrhythmias, such as sinus bradycardia; Parkinson's disease; cognitive disorders, such as Alzheimer's disease; dismenorrhea; and the like.

The amount of active agent administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the active agent and any secondary agents being administered, and the like. Treatment of a patient suffering from a disease or medical condition (such as COPD) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating COPD, significant improvement in forced expiratory volume (measured in one second) may be used to determine the effectiveness of treatment. Similar indicators for the other diseases and conditions described herein, are well-known to those skilled in the art, and are readily available to the treating physician. Continuous monitoring by the physician will insure that the optimal amount of active agent will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Accordingly, in one embodiment, compounds of the invention are useful for treating smooth muscle disorders in mammals, including humans and their companion animals (e.g., dogs, cats etc.). Such smooth muscle disorders include, by way of illustration, overactive bladder, chronic obstructive pulmonary disease and irritable bowel syndrome. Typically, suitable doses for treating smooth muscle disorders or other disorders mediated by muscarinic receptors will range from about 0.14 µg/kg/day to about 7 mg/kg/day of active agent; including from about 0.15 µg/kg/day to about 5 mg/kg/day. For an average 70 kg human, this would amount to about 10 µg per day to about 500 mg per day of active agent.

In a specific embodiment, compounds of the invention are useful for treating pulmonary or respiratory disorders, such as COPD or asthma, in mammals including humans, by administering to a patient a therapeutically effective amount of the compound. Generally, the dose for treating a pulmonary disorder will range from about 10-1500 µg/day. The term "COPD" is understood by those of ordinary skill in the art to include a variety of respiratory conditions, including chronic obstructive bronchitis and emphysema, as exemplified by the teachings of Barnes (2000) *N. Engl. J. Med.* 343:269-78, and references cited therein. When used to treat a pulmonary disorder, compounds of the invention are optionally administered in combination with other therapeutic agents such as a $\beta_2$-adrenoreceptor agonist; a corticosteroid, a non-steroidal anti-inflammatory agent, or combinations thereof.

When administered by inhalation, compounds of the invention typically have the effect of producing bronchodilation. Accordingly, in another of its method aspects, the invention relates to a method of producing bronchodilation in a patient, comprising administering to a patient a bronchodilation-producing amount of a compound of the invention. Generally, the therapeutically effective dose for producing bronchodilation will range from about 10-1500 µg/day.

In another embodiment, compounds of the invention are used to treat overactive bladder. When used to treat overactive bladder, a typical dose will range from about 1.0-500 mg/day. In yet another embodiment, compounds of the invention are used to treat irritable bowel syndrome. When used to treat irritable bowel syndrome, compounds of the invention will typically be administered orally or rectally, and a typical dose will range from about 1.0-500 mg/day.

Since compounds of this invention possess muscarinic receptor antagonist activity, such compounds are also useful as research tools for investigating or studying biological systems or samples having muscarinic receptors. Any suitable biological system or sample having $M_1$, $M_2$, $M_3$, $M_4$ and/or $M_5$ muscarinic receptors may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention a muscarinic receptor in a mammal is antagonized by administering a muscarinic receptor-antagonizing amount of a compound of the invention. Compounds of the invention can also be used as research tools by conducting biological assays using such compounds.

When used as a research tool, a biological system or sample comprising a muscarinic receptor is typically contacted with a muscarinic receptor-antagonizing amount of a compound of the invention. After the biological system or sample is exposed to the compound, the effects of antagonizing the muscarinic receptor are determined using conventional procedures and equipment, such as by measuring binding in a radioligand binding assays or ligand-mediated changes in a functional assay or by determining the amount of bronchoprotection provided by the compound in a bronchoprotection assay in a mammal. Exposure encompasses contacting cells or tissue with the compound, administering the compound to a mammal, for example by i.p. or i.v. administration, and so forth. This determining step may comprise measuring a response, i.e., a quantitative analysis or may comprise an observation, i.e., a qualitative analysis. Measuring a response involves, for example, determining the effects of the compound on the biological system or sample using conventional procedures and equipment, such as radioligand binding assays and measuring ligand-mediated changes in functional assays. The assay results can be used to determine the activity level as well as the amount of compound necessary to achieve the desired result, i.e., a muscarinic-antagonizing amount. Typically, the determining step will involve determining the muscarinic receptor ligand-mediated effects.

Additionally, compounds of the invention can be used as research tools for evaluating other chemical compounds, and thus are also useful in screening assays to discover, for example, new compounds having muscarinic receptor binding activity. In this manner, a compound of the invention is used as a standard in an assay to allow comparison of the results obtained with a test compound and with compounds of the invention to identify those test compounds that have about equal or superior binding, if any. For example, muscarinic receptor binding data (as determined, for example, by in vitro radioligand displacement assays) for a test compound or a group of test compounds is compared to the muscarinic receptor binding data for a compound of the invention to identify those test compounds that have the desired properties, e.g., test compounds having binding about equal or superior to a compound of the invention, if any. Alternatively, for example, bronchoprotective effects can be determined for test compounds and a compound of the invention in a bronchoprotection assay in a mammal and this data compared to identify test compounds providing about equal or superior bronchoprotective effects. This aspect of the invention includes, as separate embodiments, both the generation of comparison data (using the appropriate assays) and the analysis of the test data to identify test compounds of interest. Thus, a test compound can be evaluating in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include muscarinic receptor binding assays.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration. Further, the compounds of the invention may be administered, for example orally, in multiple doses per day, in a single daily dose or a single weekly dose. It will be understood that any form of the compounds of the invention, (i.e., free base, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. A "compound of the invention" may also be referred to herein as the "active agent."

The pharmaceutical compositions of this invention typically contain a therapeutically effective amount of a compound of the invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. In one embodiment, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In another embodiment, a composition suitable for inhalation, for example, comprises from about 0.01-30 wt % or active agent with yet another embodiment comprises from about 0.01-10 wt % active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for inhaled administration. Suitable compositions for inhaled administration will typically be in the form of an aerosol or a powder. Such compositions are generally administered using well-known delivery devices, such as a nebulizer inhaler, a dry powder inhaler, or a metered-dose inhaler, examples of which are described below.

In a specific embodiment of the invention, a composition comprising the active agent is administered by inhalation using a nebulizer inhaler. Such nebulizer devices typically produce a stream of high velocity air that causes the composition to spray as a mist that is carried into a patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having particles in which at least about 90 percent of the particles have a mass median diameter of less than about 10 μm. The term "mass median diameter" means the diameter such that half the mass of the particles is contained in particles with larger diameter and half is contained in particles with smaller diameter.

Suitable nebulizer devices include the Respimat® Soft Mist™ Inhaler (Boehringer Ingelheim), the AERx® Pulmonary Delivery System (Aradigm Corp.), and the PARI LC Plus Reusable Nebulizer (Pari GmbH). An exemplary composition for use in a nebulizer inhaler comprises an isotonic aqueous solution comprising from about 0.05 μg/mL to about 10 mg/mL of a compound of the invention. In one embodiment, such a solution has a pH of about 4-6.

In another specific embodiment of the invention, a composition comprising the active agent is administered by inhalation using a dry powder inhaler (DPI). Such DPIs typically administer the active agent as a free-flowing powder that is dispersed in a patient's air-stream during inspiration. In order to achieve a free flowing powder, the active agent is typically formulated with a suitable excipient such as lactose, starch, mannitol, dextrose, polylactic acid, polylactide-co-glycolide, and combinations thereof. Typically, the active agent is micronized and combined with an excipient to form a blend suitable for inhalation. Accordingly, in one embodiment of the invention, the active agent is in micronized form. For example, a representative composition for use in a DPI comprises dry lactose having a particle size between about 1 μm and about 100 μm (e.g., dry milled lactose) and micronized particles of the active agent. Such a dry powder formulation can be made, for example, by combining lactose with the active agent and then dry blending the components. Alternatively, if desired, the active agent can be formulated without an excipient. The composition is then typically loaded into a DPI, or into inhalation cartridges or capsules for use with a DPI. DPIs are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Diskus® or Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

In yet another specific embodiment of the invention, the composition comprising the active agent is administered by inhalation using a metered-dose inhaler (MDI). Such MDIs typically discharge a measured amount of the active agent using compressed propellant gas. Metered-dose formulations thus typically comprise a solution or suspension of the active agent in a liquefied propellant, such as a chlorofluorocarbon such as $CCl_3F$ or a hydrofluoroalkane (HFA) such as 1,1,1,2-tetrafluoroethane (HFA 134a) and 1,1,1,2,3,3,3-heptafluoro-n-propane (HFA 227), although HFAs are generally preferred due to concerns about chlorofluorocarbons affecting the ozone layer. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company). A representative composition for use in an MDI comprises from about 0.01-5 wt % of active agent; from about 0-20 wt % ethanol; and from about 0-5 wt % surfactant; with the remainder being an HFA propellant. Such compositions are typically prepared by adding a chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of the MDI. MDIs are well known to those of ordinary skill in the art, and many such devices are commercially available, with representative devices including AeroBid Inhaler System (Forest Pharmaceuticals), Atrovent Inhalation Aerosol (Boehringer Ingelheim), Flovent® (GlaxoSmithKline), Maxair Inhaler (3M), Proventil® Inhaler (Schering), Serevent® Inhalation Aerosol (GlaxoSmithKline), and the like. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.).

Additional examples of processes of preparing respirable particles, and formulations and devices suitable for inhalation dosing are described in U.S. Pat. No. 5,874,063 to Briggner et al.; U.S. Pat. No. 5,983,956 to Trofast; U.S. Pat. No. 6,221,398 to Jakupovic et al.; U.S. Pat. No. 6,268,533 to Gao et al.; U.S. Pat. No. 6,475,524 to Bisrat et al.; and U.S. Pat. No. 6,613,307 to Cooper.

In another embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, i.e., each unit containing a predetermined quantity of the active agent calculated to produce the desired therapeutic effect either alone or in combination with one or more additional units. For example, such unit dosage forms may be capsules, tablets, pills, and the like.

Compounds of the invention can also be administered parenterally (e.g., by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. A typical parenteral formulation is a sterile pH 4-7 aqueous solution of the active agent. Parenteral formulations may also contain one or more solubilizers, stabilizers, preservatives, wetting agents, emulsifiers, and dispersing agents. These formulations may be rendered sterile by use of a sterile injectable medium, a sterilizing agent, filtration, irradiation, or heat.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of this invention may be administered in combination with one or more other therapeutic agents. Thus, in one embodiment, compositions of the invention may optionally contain other drugs that are co-administered with a compound of the invention. For example, the composition may further comprise one or more drugs (also referred to as "secondary agents(s)") selected from the group of other bronchodilators (e.g., $PDE_3$ inhibitors, adenosine 2b modulators and $\beta_2$ adrenergic receptor agonists); anti-inflammatory agents (e.g., steroidal anti-inflammatory agents such as corticosteroids and glucocorticoids; non-steroidal anti-inflammatory agents (NSAIDs); and $PDE_4$ inhibitors); other muscarinic receptor antagonists (i.e., antichlolinergic agents); antiinfective agents (e.g., Gram positive and Gram negative antibiotics, and antiviral agents); antihistamines; protease inhibitors; afferent blockers (e.g., $D_2$ agonists and neurokinin modulators); and combinations thereof. Numerous examples of such therapeutic agents are well known in the art, and examples are described below. By combining a compound of the invention with a secondary agent, double therapy can be achieved, i.e., muscarinic receptor antagonist activity and activity associated with the secondary agent (e.g., $\beta_1$ adrenergic receptor agonist), in some cases by administering two compositions and in some cases by administering a single composition containing the active agent and the secondary agent. Accordingly, in yet another aspect of the invention, a pharmaceutical composition comprises a compound of the invention, a second active agent, and a pharmaceutically acceptable carrier. Third, fourth etc. active agents may also be included in the composition. For example, a composition may comprise a compound of the invention; a secondary agent selected from corticosteroids, $\beta_2$ adrenergic receptor agonists; phosphodiesterase-4 inhibitors, and combinations thereof; and a pharmaceutically acceptable carrier. In a specific embodiment, the composition comprises a compound of the invention, a $\beta_2$ adrenergic receptor agonist, and a steroidal anti-inflammatory agent. In combination therapy, the amount of compound of the invention that is administered, as well as the amount of secondary agents, may be less than the amount typically administered in monotherapy.

A compound of the invention may be either physically mixed with the second active agent to form a composition containing both agents; or each agent may be present in separate and distinct compositions which are administered to the patient simultaneously or sequentially. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention. In other embodiments this timed relationship is less than 12 hours, less than 8 hours, less than 6 hours, less than 4 hours, less than 3 hours, less than 1 hour, less than thirty minutes, less than ten minutes, less than one minute, or immediately after administration of the compound of the invention. This is also referred to as sequential administration. Thus, a compound of the invention can be administered by inhalation simultaneously or sequentially with another active agent using an inhalation delivery device that employs separate compartments (e.g. blister packs) for each active agent, where sequential may mean being administered immediately after administration of the compound of the invention or at some predetermined time later (e.g., one hour later or three hours later). Alternatively, the combination may be administered using separate delivery devices, i.e., one delivery device for each agent. Additionally, the agents can be delivered by different routes of administration, i.e., one by inhalation and the other by oral administration.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount. i.e., are typically administered in an amount that produces a therapeutically beneficial effect when co-administered with a compound of the invention. The secondary agent can be in the form of a pharmaceutically acceptable salt, solvate, optically pure stereoisomer, and so forth. Thus, secondary agents listed below are intended to include all such forms, and are commercially available or can be prepared using conventional procedures and reagents. Suitable doses for a secondary agent are typically in the range of about 0.05 µg/day to about 500 mg/day.

In a particular embodiment, a compound of the invention is administered in combination with a $\beta_2$ adrenergic receptor agonist. Representative $\beta_2$ adrenergic receptor agonists include, but are not limited to, albuterol, bitolterol, fenoterol, formoterol, indacaterol, isoetharine, levalbuterol, metaproterenol, pirbuterol, salbutamol, salmefamol, salmeterol, terbutaline, and the like. Other $\beta_2$ adrenergic receptor agonists that can be used in combination with compounds of the invention include, but are not limited to, 3-(4-{[6-({(2R)-2-hydroxy-2-[4-hydroxy-3-(hydroxymethyl)-phenyl]ethyl}amino)-hexyl]oxy}-butyl)benzenesulfonamide and 3-(-3-{[7-({(2R)-2-hydroxy-2-[4-hydroxy-3-(hydroxy-methyl)phenyl]ethyl}-amino)heptyl]oxy}-propyl)benzenesulfonamide and related compounds disclosed in WO 02/066422 (Glaxo Group Ltd.); 3-[3-(4-{[6-([(2R)-2-hydroxy-2-[4-hydroxy-3-(hydroxymethyl)phenyl]ethyl}amino)hexyl]oxy}butyl)phenyl]imidazolidine-2,4-dione and related compounds disclosed in WO 02/070490 (Glaxo Group Ltd.); 3-(4-{[6-({(2R)-2-[3-(formylamino)-4-hydroxyphenyl]-2-hydroxyethyl}amino)-hexyl]oxy}butyl)benzenesulfonamide, 3-(4-{[6-({(2S)-2-[3-(formylamino)-4-hydroxy-phenyl]-2-hydroxyethyl}amino)hexyl]oxy}butyl)benzenesulfonamide, 3-(4-{[6-({(2R/S)-2-[3-(formylamino)-4-hydroxyphenyl]-2-hydroxyethyl}amino)hexyl]oxy}butyl)benzene-sulfonamide, N-(t-butyl)-3-(4-{[6-({(2R)-2-[3-(formylamino)-4-hydroxyphenyl]-2-hydroxyethyl}amino)hexyl]oxy}butyl)benzenesulfonamide, N-(t-butyl)-3-(4-{[6-({(2S)-2-[3-(formylamino)-4-hydroxyphenyl]-2-hydroxyethyl}amino)hexyl]oxy}butyl)benzene-sulfonamide, N-(t-butyl)-3-(4-{[6-({(2R/S)-2-[3-(formylamino)-4-hydroxyphenyl]-2-hydroxyethyl}amino)hexyl]oxy}butyl)benzenesulfonamide and related compounds disclosed in WO 02/076933 (Glaxo Group Ltd.); 4-{(1R)-2-[(6-{2-[(2,6-dichlorobenzyl)-oxy]ethoxy}hexyl)amino]-1-hydroxyethyl}-2-(hydroxymethyl)phenol and related compounds disclosed in WO 03/024439 (Glaxo Group Ltd.); N-{2-[4-((R)-2-hydroxy-2-phenylethylamino)phenyl]ethyl}-(R)-2-hydroxy-2-(3-formamido-4-hydroxyphenyl)-ethylamine and related compounds disclosed in U.S. Pat. No. 6,576,793 to Moran et al.; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds disclosed in U.S. Pat. No. 6,653,323 to Moran et al. In a particular embodiment, the $\beta_2$-adrenoreceptor agonist is a crystalline monohydrochloride salt of N-{2-[4-((R)-2-hydroxy-2-phenylethylamino)-phenyl]ethyl}-(R)-2-hydroxy-2-(3-formamido-4-hydroxyphenyl)ethylamine. Typically, the $\beta_2$-adrenoreceptor agonist will be administered in an amount sufficient to provide from about 0.05-500 µg per dose.

In a particular embodiment, a compound of the invention is administered in combination with a steroidal anti-inflammatory agent. Representative steroidal anti-inflammatory agents include, but are not limited to, beclomethasone dipropionate; budesonide; butixocort propionate; 20R-16α,17α-[butyl-idenebis(oxy)]-6α,9α-difluoro-11β-hydroxy-17β-(methylthio)androsta-4-en-3-one (RPR-106541); ciclesonide; dexamethasone; 6α,9α-difluoro-17α-[(2-furanylcarbonyl)oxy]-11β-hydroxy-16α-methyl-3-oxoandrosta-1,4-diene-17β-carbothioic acid S-fluoromethyl ester; 6α,9α-difluoro-11β-hydroxy-16α-methyl-17α-[(4-methyl-1,3-thiazole-5-carbonyl)oxy]-3-oxoandrosta-1,4-diene-17β-carbothioic acid S-fluoromethyl ester; 6α,9α-difluoro-11β-hydroxy-16α-methyl-3-oxo-17α-propionyloxyandrosta-1,4-diene-17β-carbothioic acid (S)-(2-oxotetrahydrofuran-3S-yl) ester; flunisolide; fluticasone propionate; methyl prednisolone; mometasone furoate; prednisolone; prednisone; rofleponide; ST-126; triamcinolone acetonide; and the like. Typically, the steroidal anti-inflammatory agent will be administered in an amount sufficient to provide from about 0.05-500 µg per dose.

An exemplary combination is a compound of the invention co-administered with salmeterol as the $\beta_2$ adrenergic receptor agonist, and fluticasone propionate as the steroidal anti-inflammatory agent. Another exemplary combination is a compound of the invention co-administered with a crystalline monohydrochloride salt of N-{2-[4-((R)-2-hydroxy-2-phenylethylamino)phenyl]ethyl}-(R)-2-hydroxy-2-(3-formamido-4-hydroxyphenyl)-ethylamine as the $\beta_2$-adrenoreceptor agonist, and 6α,9α-difluoro-17α-[(2-furanylcarbonyl)oxy]-11β-hydroxy-16α-methyl-3-oxoandrosta-1,4-diene-17β-carbothioic acid S-fluoro-methyl ester as the steroidal anti-inflammatory agent.

Other suitable combinations include, for example, other anti-inflammatory agents, e.g., NSAIDs (such as sodium cromoglycate; nedocromil sodium; phosphodiesterase (PDE) inhibitors (e.g., theophylline, PDE4 inhibitors or mixed PDE3/PDE4 inhibitors); leukotriene antagonists (e.g., monteleukast); inhibitors of leukotriene synthesis; iNOS inhibitors; protease inhibitors, such as tryptase and elastase inhibitors; beta-2 integrin antagonists and adenosine receptor agonists or antagonists (e.g., adenosine 2a agonists); cytokine antagonists (e.g., chemokine antagonists such as, an interleukin antibody (αIL antibody), specifically, an αIL-4 therapy, an αIL-13 therapy, or a combination thereof); or inhibitors of cytokine synthesis.

In a particular embodiment, a compound of the invention is administered in combination with a phosphodiesterase-4 (PDE4) inhibitors or mixed PDE3/PDE4 inhibitors. Representative PDE4 or mixed PDE3/PDE4 inhibitors include, but are not limited to, cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxy-phenyl)cyclohexan-1-one; cis-[4-cyano-4-(3-cyclopropylmethoxy-4-difluoromethoxy-phenyl) cyclohexan-1-ol]; cis-4-cyano-4-[3-(cyclopentyloxy)-4-methoxyphenyl]-cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

In a particular embodiment, a compound of the invention is administered in combination with a muscarinic antagonist (i.e., anticholinergic agent). Representative muscarinic antagonists include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like.

In a particular embodiment, a compound of the invention is administered in combination with an antihistamine (i.e., $H_1$-receptor antagonist). Representative antihistamines include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like.

The following formulations illustrate representative pharmaceutical compositions of the invention.

Exemplary Compositions for Administration by a DPI

A compound of the invention (0.2 mg) is micronized and then blended with lactose (25 mg). This blended mixture is then loaded into a gelatin inhalation cartridge. The contents of the cartridge are administered using a DPI, for example.

A micronized compound of the invention (100 mg) is blended with milled lactose (25 g) (e.g., lactose in which not greater than about 85% of the particles have a MMD of about 60 μm to about 90 μm and not less than 15% of the particles have a MMD of less then 15 μm). This blended mixture is then loaded into individual blisters of a peelable blister pack in an amount sufficient to provide about 10 μg to about 500 μg of the compound of the invention per dose. The contents of the blisters are administered using a DPI.

Alternately, a micronized compound of the invention (1 g) is blended with milled lactose (200 g) to form a bulk composition having a weight ratio of compound to milled lactose of 1:200. The blended composition is packed into a DPI capable of delivering between about 10 μg to about 500 μg of the compound of the invention per dose.

Alternately, a micronized compound of the invention (100 mg) and a micronized $\beta_2$ adrenergic receptor agonist (500 mg) are blended with milled lactose (30 g). The blended mixture is then loaded into individual blisters of a peelable blister pack in an amount sufficient to provide about 10 μg to about 500 μg of the compound of the invention per dose. The contents of the blisters are administered using a DPI.

Exemplary Compositions for Use in an MDI

A micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into MDI cartridges containing pressurized 1,1,1,2-tetrafluoroethane in an amount sufficient to provide about 10 μg to about 500 μg of the compound of the invention per dose when administered by the MDI.

Alternately, a suspension containing 5 wt % compound of the invention, 0.5 wt % lecithin, and 0.5 wt % trehalose is prepared by dispersing 5 g of a compound of the invention as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Exemplary Composition for Use in a Nebulizer Inhaler

A compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the compound of the invention per dose.

Exemplary Hard Gelatin Capsules for Oral Administration

A compound of the invention (50 g), spray-dried lactose (440 g) and magnesium stearate (10 g) are thoroughly blended. The resulting composition is then loaded into hard gelatin capsules (500 mg of composition per capsule).

Exemplary Suspension for Oral Administration

The following ingredients are mixed to form a suspension containing 100 mg of compound per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard meaning:

| AC | adenylyl cyclase |
| --- | --- |
| BSA | bovine serum albumin |
| cAMP | 3'-5' cyclic adenosine monophosphate |
| CHO | Chinese hamster ovary |
| $cM_5$ | cloned chimpanzee $M_5$ receptor |
| DCM | dichloromethane (i.e., methylene chloride) |
| DIPEA | N,N-diisopropylethylamine |
| dPBS | Dulbecco's phosphate buffered saline |
| DMF | N,N-dimethylformamide |
| EDCI | N-(3-dimethylaminopropyl)-N'-ethylcarbodiimide |
| EDTA | ethylenediamine tetraacetic acid |
| EtOAc | ethyl acetate |
| FBS | fetal bovine serum |
| FLIPR | fluorometric imaging plate reader |
| HBSS | Hank's Buffered Salt Solution |
| HEPES | 4-(2-hydroxyethyl)-1-piperazineethanesulfonic acid |
| $hM_1$ | cloned human $M_1$ receptor |
| $hM_2$ | cloned human $M_2$ receptor |
| $hM_3$ | cloned human $M_3$ receptor |
| $hM_4$ | cloned human $M_4$ receptor |
| $hM_5$ | cloned human $M_5$ receptor |
| HOBt | 1-hydroxybenzotriazole hydrate |
| MCh | methylcholine |
| MeOH | methanol |
| TFA | trifluoroacetic acid |
| THF | tetrahydrofuran |

Any other abbreviations used herein but not defined have their standard, generally accepted meaning. Unless noted otherwise, all materials, such as reagents, starting materials and solvents, were purchased from commercial suppliers (such as Sigma-Aldrich, Fluka Riedel-de Haën, and the like) and were used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC.

Preparation 1

(R)-cyclopentylhydroxyphenyl Acetic Acid

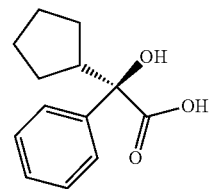

(2R,5R)-2-t-Butyl-5-phenyl-1,3-dioxolan-4-one (1a): (R)-Mandelic acid (20 g, 130 mmol) was dissolved in anhydrous pentane (200 mL, 1.7 mol). Pivaldehyde (13.6 g, 153 mmol) was added followed by trifluoromethanesulfonic acid (488 μL, 5.4 mmol). The reaction was allowed to reflux at 36° C. under nitrogen. After 5.5 hours, the mixture was allowed to cool to room temperature before stirring with 200 mL of an 8 wt % NaHCO$_3$ solution for 10 minutes. Excess pentane was removed by rotary evaporation. The solids were collected by filtration and rinsed (100 mL water) while under vacuum filtration. The solids were dried overnight under high vacuum to yield intermediate (1a) as a white solid (23.8 g, 88% purity).

(2R,5S)-2-t-Butyl-5-(1-hydroxycyclopentyl)-5-phenyl-1, 3-dioxolan-4-one (1b): Lithium hexamethyldisilazide (0.8 g, 4.7 mmol; 4.7 mL of 1.0 M in hexanes) was added to anhydrous THF (5.3 mL, 65 mmol) at −78° C. Intermediate (1a) (800 mg, 3.6 mmol) in 5.3 mL anhydrous THF was added to the solution dropwise over 15 minutes. After 30 minutes cyclopentanone (451 μL, 5.1 mmol) was added dropwise over less than 1 minute. After 2 hours, 0.8 mL of saturated aqueous Na₂HPO₄ was added, and the mixture stirred at room temperature for 5 minutes. The mixture was added to 8 mL saturated aqueous ammonium chloride. The aqueous layer was washed (2×80 mL EtOAc), and the organic layers were combined, dried over Na₂SO₄, filtered and concentrated. The crude product (780 mg) was purified by flash chromatography (5-15% EtOAc gradient over 30 minutes with hexanes) to yield intermediate (1b).

(2R,5S)-2-t-Butyl-5-cyclopent-1-enyl-5-phenyl-1,3-dioxolan-4-one (1c): Intermediate (1b) (650 mg, 2.1 mmol) was dissolved in 6.8 mL anhydrous THF and the solution was cooled to 0° C. Thionyl chloride (436 μL, 6 mmol) was added dropwise, followed by the addition of pyridine (777 μL, 9.6 mmol). The mixture was stirred at 0° C. for 1 hour. Saturated aqueous ammonium chloride (14 mL) was added and the mixture was stirred for 5 minutes while warming to room temperature. The layers were separated, and the aqueous layer was washed (2×100 mL EtOAc.). The organic layers were combined, dried over Na₂SO₄, filtered and concentrated to yield intermediate (1c) as a light yellow oil (540 mg), which was used in the next step without further purification.

(S)-Cyclopent-1-enyl-hydroxyphenylacetic acid (1d): Intermediate (1c) (540 mg, 1.9 mmol) was dissolved in MeOH (927 μL, 22.9 mmol). Water (1.84 mL, 102 mmol) was added, followed by the addition of KOH (1.1 g, 18.8 mmol). The reaction was refluxed at 130° C. for 3 hours. The mixture was diluted to 250 mL with saturated ammonium chloride, then washed (2×100 mL hexane). The remaining aqueous emulsion was washed (2×250 mL EtOAc). The EtOAc layers were combined, washed with 50 mL saturated aqueous NaCl, dried over Na₂SO₄, filtered and concentrated to yield intermediate (1d) as a brownish-yellow solid (290 mg).

Intermediate (1d) (280 mg, 1.3 mmol) was dissolved in MeOH (2.50 mL, 61.7 mmol) and the reaction flask was flushed with nitrogen before 28 mg of 10% Pd/C was added to the mixture. The mixture was stirred at room temperature under 1 atm hydrogen and the reaction was monitored by HPLC until the starting material was consumed (~24 hours). The reaction vessel was flushed with nitrogen, then the mixture was filtered through celite and rinsed with MeOH. The filtrate was concentrated under vacuum to obtain the title compound as a slightly yellow solid (284 mg).

Preparation 2

(R)-2-Cyclopentyl-2-hydroxy-2-phenyl-1-piperazin-1-ylethanone

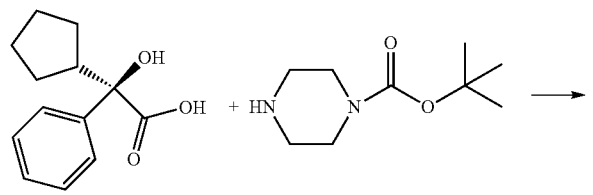

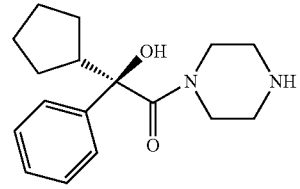

To a stirred solution of (R)-cyclopentylhydroxyphenyl acetic acid (10.0 g, 45.4 mmol) in DCM (200 mL) was added t-butyl 1-piperazinecarboxylate (8.5 g, 45.4 mmol). Into the reaction was added DIPEA (23.7 mL, 13.6 mmol), HOBt (10.4 g, 68.1 mmol), and then EDCI (10.4 g, 54.5 mmol). The mixture was stirred at room temperature for 12 hours. The mixture was then washed with 1N NaOH (300 mL), 1N HCl (300 mL) then saturated aqueous NaCl (300 mL). The organic layer was then removed, dried over MgSO₄ and then filtered. The solvent was removed under reduced pressure. A solution of 20% TFA/DCM was added to the crude material, and the resulting mixture was stirred for 2 hours at room temperature. The solvent was removed under reduced pressure. DCM (300 mL) was added and the mixture was washed with saturated sodium bicarbonate (300 mL). The organic layer was then removed, dried over MgSO₄ and filtered. The crude material was purified via silica gel chromatography (10% MeOH/DCM w/1% NH₃ (aq)) to afford the title compound as a white powder (9.0 g, 31.2 mmol).

Example 1

4-((R)-2-Cyclopentyl-2-hydroxy-2-phenylacetyl)—N-thiophen-2-ylmethylpiperazine-1-carboxamidine

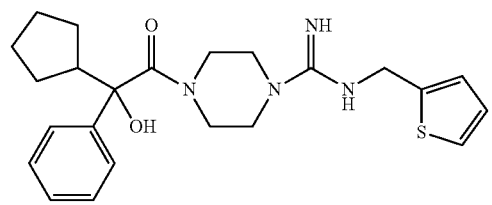

To a stirred solution of (R)-2-cyclopentyl-2-hydroxy-2-phenyl-1-piperazin-1-ylethanone (3.9 g 13.7 mmol) in DMF (200 mL) was added DIPEA (4.8 mL, 27.3 mmol), and then C-(bis-benzotriazol-1-yl)methylene amine (3.6 g, 13.7 mmol). This was stirred at room temperature for 30 minutes, followed by the addition of C-thiophen-2-yl-methylamine (2.8 mL, 27.3 mmol). The mixture was heated at 60° C. for ~14 hours. The reaction was cooled to room temperature and the solvent removed by reduced pressure. The crude material was purified by reverse phase-HPLC to afford the title compound as a TFA salt (0.7 g, 1.3 mmol). MS m/z: [M+H]⁺calcd for C₂₃H₃₀N₄O₂S, 427.21. found 427.2.

Alternate Synthesis

DIPEA (7.3 mL, 41.6 mmol) was added to (R)-2-cyclopentyl-2-hydroxy-2-phenyl-1-piperazin-1-ylethanone (6.0 g, 20.8 mmol) dissolved in ethanol (90 mL, 2 mol). C-(bis-benzotriazol-1-yl)-methyleneamine (6.0 g, 22.9 mmol) was added and the mixture stirred at room temperature for 30 minutes. C-Thiophen-2-yl-methylamine (4.9 g, 41.6 mmol)

was added and the mixture was stirred overnight at 55° C. The mixture was condensed and the product purified by HPLC to afford the title compound as a TFA salt (7.3 g, 98% purity). MS m/z: [M+H]⁺calcd for $C_{23}H_{30}N_4O_2S$, 427.21. found 427.4.

Example 2

4-((R)-2-Cyclopentyl-2-hydroxy-2-phenylacetyl)—N-(4-hydroxybenzyl)piperazine-1-carboxamidine

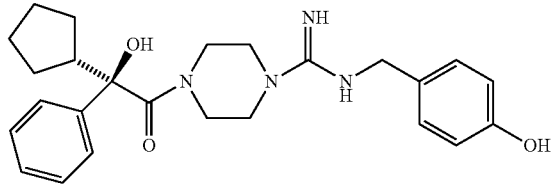

To a stirred solution of (R)-2-cyclopentyl-2-hydroxy-2-phenyl-1-piperazin-1-ylethanone (5.00 g 17.3 mmol; prepared as described in Preparation 1) in DMF (200 mL) was added DIPEA (10.6 mL, 60.7 mmol) and then C-(bis-benzotriazol-1-yl)-methylene amine (5.48 g, 20.8 mmol). This was stirred at room temperature for 30 minutes, followed by the addition of 4-hydroxybenzyl amine (12.0 g mL, 97 mmol). The mixture was heated at 60° C. for ~14 hours. The reaction was cooled to room temperature and the solvent removed by reduced pressure. The crude material was purified by reverse phase-HPLC to afford the title compound as a TFA salt (1.7 g, 3.1 mmol). MS m/z: [M+H]⁺calcd for $C_{25}H_{32}N_4O_3$, 437.25. found 437.2.

Example 3

4-((R)-2-Cyclopentyl-2-hydroxy-2-phenylacetyl)-N-furan-2-ylmethylpiperazine-1-carboxamidine

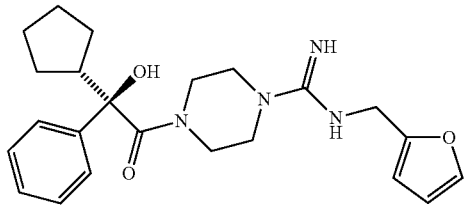

(R)-2-Cyclopentyl-2-hydroxy-2-phenyl-1-piperazin-1-ylethanone (2.0 g, 6.9 mmol) and C-(bis-benzotriazol-1-yl) methyleneamine (2.0 g, 7.6 mmol) were added to ethanol (40.0 mL, 685 mmol), followed by the addition of DIPEA (2.4 mL, 13.9 mmol). The resulting mixture was stirred at room temperature for about 1 hour until all solids were dissolved, to form the intermediate. Furfurylamine (1.2 mL, 13.9 mmol) was added and the reaction mixture was stirred at 35° C. until the reaction was complete (about 22 hours). Purification by preparative HPLC yielded the title compound as a TFA salt (329 mg, 6.9 mmol, 97.5% purity). MS m/z: [M+H]⁺ calcd for $C_{23}H_{30}N_4O_3$, 411.23. found 411.2.

Example 4

Following the procedures described in the previous examples, and substituting the appropriate starting materials and reagents, compounds 4-1 to 4-52, having the following, were also prepared as TFA salts:

[structure image with cyclopentyl, OH, phenyl, piperazine, and NH-Z carboxamidine scaffold]

| Ex. | Z | Q |
|---|---|---|
| 4-1 | —CH(CH₃)—Q | phenyl |
| 4-2 | —CH₂—Q | 3,4-difluorophenyl |
| 4-3 | —CH₂—Q | 4-methoxyphenyl |
| 4-4 | —CH₂—Q | thiophen-3-yl |
| 4-5 | —CH₂—Q | phenyl |
| 4-6 | —CH₂—Q | 3-fluorophenyl |
| 4-7 | —(CH₂)₂—Q | phenyl |
| 4-8 | —CH₂—Q | pyridin-2-yl |
| 4-9 | —CH₂—Q | 3-hydroxyphenyl |
| 4-10 | —CH₂—Q | 4-fluorophenyl |
| 4-11 | —CH₂—Q | 2-fluorophenyl |
| 4-12 | —CH₂—Q | cyclohexyl |
| 4-13 | —CH₂—Q | 3-methoxyphenyl |
| 4-14 | —CH₂—Q | 3,5-difluorophenyl |
| 4-15 | —CH₂—Q | thiazol-2-yl |
| 4-16 | —CH₂—Q | 1H-pyrazol-3-yl |
| 4-17 | —NH—Q | phenyl |
| 4-18 | —CH₂—Q | furan-3-yl |
| 4-19 | —CH₂—Q | 2-methyl-thiazol-4-yl |
| 4-20 | —CH₂—Q | propyl |
| 4-21 | —CH₂—Q | butyl |
| 4-22 | —CH₂—Q | pentyl |
| 4-23 | —NH—Q | 2-fluorophenyl |
| 4-24 | —NH—Q | 2-chlorophenyl |
| 4-25 | —NH—Q | 3-fluorophenyl |
| 4-26 | —NH—Q | 3-chlorophenyl |
| 4-27 | —NH—Q | 4-methylphenyl |
| 4-28 | —NH—Q | 4-fluorophenyl |
| 4-29 | —NH—Q | 4-chlorophenyl |
| 4-30 | —NH—Q | 4-methoxyphenyl |
| 4-31 | —CH₂—Q | 4-benzoic acid methyl ester |
| 4-32 | —CH₂—Q | 1H-indol-2-yl |
| 4-33 | —CH₂—Q | cycloheptyl |
| 4-34 | —CH₂—Q | 2-hydroxyphenyl |
| 4-35 | —CH₂—Q | 4-trifluoromethoxyphenyl |
| 4-36 | —CH₂—Q | 4-amidophenyl |
| 4-37 | —CH₂—Q | 4-hydroxymethylphenyl |
| 4-38 | —CH₂—Q | 1H-indol-5-yl |
| 4-39 | —CH₂—Q | benzofuran-5-yl |
| 4-40 | —CH₂—Q | 4-methylphenyl |
| 4-41 | —CH₂—Q | 4-methylsulfanylphenyl |
| 4-42 | —CH₂—Q | 3-cyanophenyl |
| 4-43 | —CH₂—Q | 3-amidophenyl |
| 4-44 | —CH₂—Q | 2-methylphenyl |
| 4-45 | —CH₂—Q | 3-methylphenyl |
| 4-46 | —CH₂—Q | 1H-indol-4-yl |
| 4-47 | —CH₂—Q | 3-methylsulfanylphenyl |
| 4-48 | —CH₂—Q | benzo[b]thiophen-5-yl |
| 4-49 | —CH₂—Q | benzo[1,3]dioxo1-5-yl |
| 4-50 | —CH₂—Q | benzo[b]thiophen-2-yl |
| 4-51 | —CH₂—Q | 1-methyl-1H-pyrazol-3-yl |
| 4-52 | —CH₂—Q | cyclopentyl |

(4-1) 4-(2-cyclopentyl-2-hydroxy-2-phenylacetyl)-N—((R)-1-phenylethyl)piperazine-1-carboxamidine. MS m/z: [M+H]⁺calcd for $C_{26}H_{34}N_4O_2$, 435.27. found 435.2.

(4-2) 4-(2-cyclopentyl-2-hydroxy-2-phenylacetyl)-N-(3,4-difluorobenzyl)piperazine-1-carboxamidine. MS m/z: [M+H]⁺calcd for $C_{25}H_{30}F_2N_4O_2$, 457.23. found 457.2.

(4-3) 4-(2-cyclopentyl-2-hydroxy-2-phenylacetyl)-N-(4-methoxybenzyl)piperazine-1-carboxamidine. MS m/z: [M+H]⁺calcd for $C_{26}H_{34}N_4O_3$, 451.26. found 451.2.

(4-4) 4-((R)-2-cyclopentyl-2-hydroxy-2-phenylacetyl)-N-thiophen-3-ylmethyl-piperazine-1-carboxamidine. MS m/z: [M+H]$^+$calcd for $C_{23}H_{30}N_4O_2S$, 427.21. found 427.4.

(4-5) N-benzyl-4-((R)-2-cyclopentyl-2-hydroxy-2-phenylacetyl)piperazine-1-carboxamidine. MS m/z: [M+H]$^+$ calcd for $C_{25}H_{32}N_4O_2$, 421.25. found 421.2.

(4-6) 4-((R)-2-cyclopentyl-2-hydroxy-2-phenylacetyl)-N-(3-fluorobenzyl)piperazine-1-carboxamidine. MS m/z: [M+H]$^+$calcd for $C_{25}H_{31}FN_4O_2$, 439.24. found 439.2.

(4-7) 4-((R)-2-cyclopentyl-2-hydroxy-2-phenylacetyl)-N-phenethylpiperazine-1-carboxamidine. MS m/z: [M+H]$^+$ calcd for $C_{26}H_{34}N_4O_2$, 435.27. found 435.2.

(4-8) 4-((R)-2-cyclopentyl-2-hydroxy-2-phenylacetyl)-N-pyridin-2-ylmethyl-piperazine-1-carboxamidine. MS m/z: [M+H]$^+$calcd for $C_{24}H_{31}N_5O_2$, 422.25. found 422.2.

(4-9) 4-((R)-2-cyclopentyl-2-hydroxy-2-phenylacetyl)-N-(3-hydroxybenzyl)piperazine-1-carboxamidine. MS m/z: [M+H]$^+$calcd for $C_{25}H_{32}N_4O_3$, 437.25. found 437.2.

(4-10) 4-((R)-2-cyclopentyl-2-hydroxy-2-phenylacetyl)-N-(4-fluorobenzyl)piperazine-1-carboxamidine. MS m/z: [M+H]$^+$calcd for $C_{25}H_{31}FN_4O_2$, 439.24. found 439.2.

(4-11) 4-((R)-2-cyclopentyl-2-hydroxy-2-phenylacetyl)-N-(2-fluorobenzyl)piperazine-1-carboxamidine. MS m/z: [M+H]$^+$calcd for $C_{25}H_{31}FN_4O_2$, 439.24. found 439.2.

(4-12) N-cyclohexylmethyl-4-((R)-2-cyclopentyl-2-hydroxy-2-phenylacetyl)piperazine-1-carboxamidine. MS m/z: [M+H]$^+$calcd for $C_{25}H_{38}N_4O_2$, 427.30. found 427.2.

(4-13) 4-((R)-2-cyclopentyl-2-hydroxy-2-phenylacetyl)-N-(3-methoxybenzyl)piperazine-1-carboxamidine. MS m/z: [M+H]$^+$calcd for $C_{26}H_{34}N_4O_3$, 451.26. found 451.2.

(4-14) 4-((R)-2-cyclopentyl-2-hydroxy-2-phenylacetyl)-N-(3,5-difluorobenzyl)-piperazine-1-carboxamidine. MS m/z: [M+H]$^+$calcd for $C_{25}H_{30}F_2N_4O_2$, 457.23. found 457.2.

(4-15) 4-((R)-2-cyclopentyl-2-hydroxy-2-phenylacetyl)-N-thiazol-2-ylmethyl-piperazine-1-carboxamidine. MS m/z: [M+H]$^+$calcd for $C_{22}H_{29}N_5O_2S$, 428.20. found 428.2.

(4-16) 4-((R)-2-cyclopentyl-2-hydroxy-2-phenylacetyl)-N-(1H-pyrazol-3-ylmethyl)piperazine-1-carboxamidine. MS m/z: [M+H]$^+$calcd for $C_{22}H_{30}N_6O_2$, 411.24. found 411.2.

(4-17) 4-((R)-2-cyclopentyl-2-hydroxy-2-phenylacetyl)-N-(phenylamino)piperazine-1-carboxamidine. MS m/z: [M+H]$^+$calcd for $C_{24}H_{31}N_5O_2$, 422.25. found 422.2.

(4-18) 4-((R)-2-cyclopentyl-2-hydroxy-2-phenylacetyl)-N-furan-3-ylmethylpiperazine-1-carboxamidine. MS m/z: [M+H]$^+$calcd for $C_{23}H_{30}N_4O_3$, 411.23. found 411.2.

(4-19) 4-((R)-2-cyclopentyl-2-hydroxy-2-phenylacetyl)-N-(2-methylthiazol-4-ylmethyl)piperazine-1-carboxamidine. MS m/z: [M+H]$^+$calcd for $C_{23}H_{31}N_5O_2S$, 442.22. found 442.2.

(4-20) N-butyl-4-((R)-2-cyclopentyl-2-hydroxy-2-phenylacetyl)-piperazine-1-carboxamidine. MS m/z: [M+H]$^+$ calcd for $C_{22}H_{34}N_4O_2$, 387.27. found 387.2.

(4-21) 4-((R)-2-cyclopentyl-2-hydroxy-2-phenylacetyl)-N-pentylpiperazine-1-carboxamidine. MS m/z: [M+H]$^+$ calcd for $C_{23}H_{36}N_4O_2$, 401.28. found 401.2.

(4-22) 4-((R)-2-cyclopentyl-2-hydroxy-2-phenylacetyl)-N-hexylpiperazine-1-carboxamidine. MS m/z: [M+H]$^+$calcd for $C_{24}H_{38}N_4O_2$, 415.30. found 415.2.

(4-23) 4-((R)-2-cyclopentyl-2-hydroxy-2-phenylacetyl)-N-(2-fluorophenyl)piperazine-1-carboxamidine. MS m/z: [M+H]$^+$calcd for $C_{24}H_{30}FN_5O_2$, 440.24. found 440.2.

(4-24) 4-((R)-2-cyclopentyl-2-hydroxy-2-phenylacetyl)-N-(2-chlorophenyl)piperazine-1-carboxamidine. MS m/z: [M+H]$^+$calcd for $C_{24}H_{30}ClN_5O_2$, 456.21. found 456.2.

(4-25) 4-((R)-2-cyclopentyl-2-hydroxy-2-phenylacetyl)-N-(3-fluorophenyl)piperazine-1-carboxamidine. MS m/z: [M+H]$^+$calcd for $C_{24}H_{30}FN_5O_2$, 440.24. found 440.2.

(4-26) 4-((R)-2-cyclopentyl-2-hydroxy-2-phenylacetyl)-N-(3-chlorophenyl)piperazine-1-carboxamidine. MS m/z: [M+H]$^+$calcd for $C_{24}H_{30}ClN_5O_2$, 456.21. found 456.2.

(4-27) 4-((R)-2-cyclopentyl-2-hydroxy-2-phenylacetyl)-N-(4-methylphenyl)piperazine-1-carboxamidine. MS m/z: [M+H]$^+$calcd for $C_{25}H_{33}N_5O_2$, 436.26. found 436.2.

(4-28) 4-((R)-2-cyclopentyl-2-hydroxy-2-phenylacetyl)-N-(4-fluorophenyl)piperazine-1-carboxamidine. MS m/z: [M+H]$^+$calcd for $C_{24}H_{30}FN_5O_2$, 440.24. found 440.2.

(4-29) 4-((R)-2-cyclopentyl-2-hydroxy-2-phenylacetyl)-N-(4-chlorophenyl)piperazine-1-carboxamidine. MS m/z: [M+H]$^+$calcd for $C_{24}H_{30}ClN_5O_2$, 456.21. found 456.2.

(4-30) 4-((R)-2-cyclopentyl-2-hydroxy-2-phenylacetyl)-N-(4-methoxyphenyl)-piperazine-1-carboxamidine. MS m/z: [M+H]$^+$calcd for $C_{25}H_{33}N_5O_3$, 452.26. found 452.2.

(4-31) 4-({[4-((R)-2-cyclopentyl-2-hydroxy-2-phenylacetyl)piperazine-1-carboximidoyl]amino}methyl)benzoic acid methyl ester. MS m/z: [M+H]$^+$calcd for $C_{27}H_{34}N_4O_4$, 479.26. found 479.2.

(4-32) 4-((R)-2-cyclopentyl-2-hydroxy-2-phenylacetyl)-N-(1H-indol-2-ylmethyl)piperazine-1-carboxamidine. MS m/z: [M+H]$^+$calcd for $C_{27}H_{33}N_5O_2$, 460.26. found 460.2.

(4-33) N-cycloheptylmethyl-4-((R)-2-cyclopentyl-2-hydroxy-2-phenylacetyl)piperazine-1-carboxamidine. MS m/z: [M+H]$^+$calcd for $C_{26}H_{40}N_4O_2$, 441.32. found 441.2.

(4-34) 4-((R)-2-cyclopentyl-2-hydroxy-2-phenylacetyl)-N-(2-hydroxybenzyl)piperazine-1-carboxamidine. MS m/z: [M+H]$^+$calcd for $C_{25}H_{32}N_4O_3$, 437.25. found 437.2.

(4-35) 4-((R)-2-cyclopentyl-2-hydroxy-2-phenylacetyl)-N-(4-trifluoromethoxybenzyl)piperazine-1-carboxamidine. MS m/z: [M+H]$^+$calcd for $C_{26}H_{31}F_3N_4O_3$, 505.24. found 505.2.

(4-36) 4-({[4-((R)-2-cyclopentyl-2-hydroxy-2-phenylacetyl)piperazine-1-carboximidoyl]amino}methyl)benzamide. MS m/z: [M+H]$^+$calcd for $C_{26}H_{33}N_5O_3$, 464.26. found 464.2.

(4-37) 4-((R)-2-cyclopentyl-2-hydroxy-2-phenylacetyl)-N-(4-hydroxymethylbenzyl)-piperazine-1-carboxamidine. MS m/z: [M+H]$^+$calcd for $C_{26}H_{34}N_4O_3$, 451.26. found 451.2.

(4-38) 4-((R)-2-cyclopentyl-2-hydroxy-2-phenylacetyl)-N-(1H-indol-5-ylmethyl)-piperazine-1-carboxamidine. MS m/z: [M+H]$^+$calcd for $C_{27}H_{33}N_5O_2$, 460.26. found 460.2.

(4-39) N-benzofuran-5-ylmethyl-4-((R)-2-cyclopentyl-2-hydroxy-2-phenylacetyl)-piperazine-1-carboxamidine. MS m/z: [M+H]$^+$calcd for $C_{27}H_{32}N_4O_3$, 461.25. found 461.2.

(4-40) 4-((R)-2-cyclopentyl-2-hydroxy-2-phenylacetyl)-N-(4-methylbenzyl)-piperazine-1-carboxamidine. MS m/z: [M+H]$^+$calcd for $C_{26}H_{34}N_4O_2$, 435.27. found 435.2.

(4-41) 4-((R)-2-cyclopentyl-2-hydroxy-2-phenylacetyl)-N-(4-methylsulfanylbenzyl)-piperazine-1-carboxamidine. MS m/z: [M+H]$^+$calcd for $C_{26}H_{34}N_4O_2S$, 467.24. found 467.2.

(4-42) N-(3-cyanobenzyl)-4-((R)-2-cyclopentyl-2-hydroxy-2-phenylacetyl)piperazine-1-carboxamidine. MS m/z: [M+H]$^+$calcd for $C_{26}H_{31}N_5O_2$, 446.25. found 446.2.

(4-43) 3-({[4-((R)-2-cyclopentyl-2-hydroxy-2-phenylacetyl)-piperazine-1-carboximidoyl]amino}methyl)benzamide. MS m/z: [M+H]$^+$calcd for $C_{26}H_{33}N_5O_3$, 464.26. found 464.2.

(4-44) 4-((R)-2-cyclopentyl-2-hydroxy-2-phenylacetyl)-N-(2-methylbenzyl)-piperazine-1-carboxamidine. MS m/z: [M+H]$^+$calcd for $C_{26}H_{34}N_4O_2$, 435.27. found 434.2.

(4-45) 4-((R)-2-cyclopentyl-2-hydroxy-2-phenylacetyl)-N-(3-methylbenzyl)-piperazine-1-carboxamidine. MS m/z: [M+H]$^+$calcd for $C_{26}H_{34}N_4O_2$, 435.27. found 435.2.

(4-46) 4-((R)-2-cyclopentyl-2-hydroxy-2-phenylacetyl)-N-(1H-indol-4-ylmethyl)-piperazine-1-carboxamidine. MS m/z: [M+H]$^+$calcd for $C_{27}H_{33}N_5O_2$, 460.26. found 460.2.

(4-47) 4-((R)-2-cyclopentyl-2-hydroxy-2-phenylacetyl)-N-(3-methylsulfanylbenzyl)-piperazine-1-carboxamidine. MS m/z: [M+H]+calcd for $C_{26}H_{34}N_4O_2S$, 467.24. found 467.2.

(4-48) N-benzo[b]thiophen-5-ylmethyl-4-((R)-2-cyclopentyl-2-hydroxy-2-phenyl-acetyl)piperazine-1-carboxamidine. MS m/z: [M+H]+calcd for $C_{27}H_{32}N_4O_2S$, 477.22. found 477.2.

(4-49) N-benzo[1,3]dioxol-5-ylmethyl-4-((R)-2-cyclopentyl-2-hydroxy-2-phenyl-acetyl)piperazine-1-carboxamidine. MS m/z: [M+H]+calcd for $C_{26}H_{32}N_4O_4$, 465.24. found 465.2.

(4-50) N-benzo[b]thiophen-2-ylmethyl-4-((R)-2-cyclopentyl-2-hydroxy-2-phenylacetyl)piperazine-1-carboxamidine. MS m/z: [M+H]+calcd for $C_{27}H_{32}N_4O_2S$, 477.22. found 477.2.

(3-51) 4-((R)-2-cyclopentyl-2-hydroxy-2-phenylacetyl)-N-(1-methyl-1H-pyrazol-3-ylmethyl)piperazine-1-carboxamidine. MS m/z: [M+H]+calcd for $C_{23}H_{32}N_6O_2$, 425.26. found 425.2.

(3-52) 4-((R)-2-cyclopentyl-2-hydroxy-2-phenylacetyl)-N-cyclopentylmethyl-piperazine-1-carboxamidine. MS m/z: [M+H]+calcd for $C_{24}H_{36}N_4O_2$, 413.28. found 413.2.

Example 5

Following the procedures described in the previous examples, and substituting the appropriate starting materials and reagents, compounds 5-1 and 5-2, having the following, were also prepared as TFA salts:

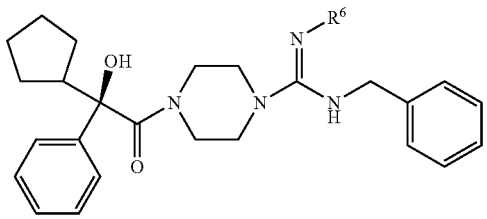

(5-1) N-benzyl-4-((R)-2-cyclopentyl-2-hydroxy-2-phenylacetyl)-N'-methyl-piperazine-1-carboxamidine ($R^6$=CH_3). MS m/z: [M+H]+calcd for $C_{26}H_{34}N_4O_2$, 435.27. found 435.2.

(5-2) N-benzyl-4-((R)-2-cyclopentyl-2-hydroxy-2-phenylacetyl)-N'-ethylpiperazine-1-carboxamidine ($R^6$=CH_2CH_3). MS m/z: [M+H]+calcd for $C_{27}H_{36}N_4O_2$, 449.28. found 449.2.

Preparation 3

(R)-3-((R)-2-Cyclopentyl-2-hydroxy-2-phenylacetoxy)pyrrolidine-1-carboxylic acid t-butyl ester

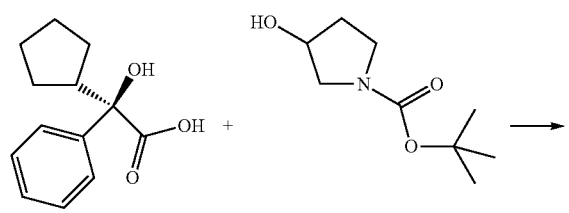

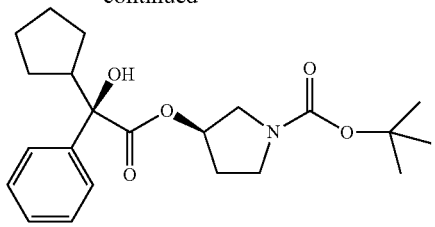

At room temperature, diisopropyl azodicarboxylate (980 µl, 5 mmol) was slowly added to a mixture of (R)-cyclopentylhydroxyphenylacetic acid (1.1 g, 5 mmol), (R)-3-hydroxy-pyrrolidine-1-carboxylic acid t-butyl ester (1.0 g, 5.5 mmol), and triphenyl-phosphine (1.3 g, 5 mmol) in 10 ml of THF. The reaction mixture was then stirred at room temperature overnight.

The solvent was removed and 100 ml of EtOAc was added. The organic layer was washed with a sodium bicarbonate solution (50 ml×3), then saturated aqueous NaCl, and dried over sodium sulfate. The solvent was removed, providing 4 g of crude product, which was purified by flash chromatography (EtOAc/hexane) to yield the title compound (1.5 g, 99% purity).

Preparation 4

(R)-Cyclopentylhydroxyphenylacetic acid (R)-pyrrolidin-3-yl ester

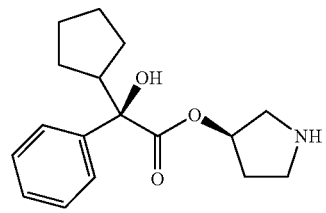

(R)-3-((R)-2-Cyclopentyl-2-hydroxy-2-phenylacetoxy) pyrrolidine-1-carboxylic acid t-butyl ester (1.3 g) in 8 ml 1,4-dioxane was added to 4 ml of 4M HCl in 1,4-dioxane and stirred at room temperature overnight to yield the title compound as an HCl salt (1 g).

Example 6

(R)-Cyclopentylhydroxyphenylacetic acid (R)-1-(N-benzylcarbamimidoyl)pyrrolidin-3-yl ester

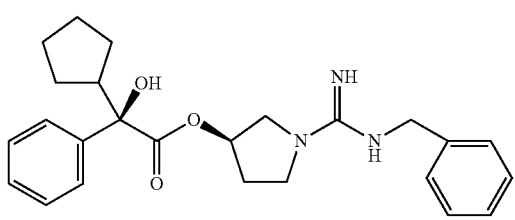

(R)-3-((R)-2-Cyclopentyl-2-hydroxy-2-phenylacetoxy) pyrrolidine-1-carboxylic acid t-butyl ester (97.5 mg, 0.3 mmol) in 3 ml of DMF was added to DIPEA (130 μl, 750 μmol), followed by the addition of C-(bis-benzotriazol-1-yl)-methyleneamine (87 mg, 330 μmol). The reaction mixture was stirred at room temperature for 2 hours, followed by the addition of benzylamine (39 μl, 360 μmol). The reaction mixture was the stirred at room temperature overnight. The solvent was removed and the solute purified by reverse phase chromatography to yield the title compound as a TFA salt (78.2 mg, 99.5% purity). MS m/z: [M+H]$^+$calcd for $C_{25}H_{31}N_3O_3$, 422.24. found 422.2.

Example 7

Following the procedures described in the previous example, and substituting the appropriate starting materials and reagents, compounds 7-1 to 7-18, having the following formula, were also prepared as TFA salts:

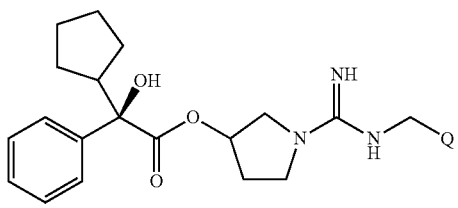

| Ex. | Q |
|---|---|
| 7-1 | phenyl |
| 7-2 | thiophen-2-yl |
| 7-3 | 2-hydroxyphenyl |
| 7-4 | 3-hydroxyphenyl |
| 7-5 | 4-hydroxyphenyl |
| 7-6 | furan-2-yl |
| 7-7 | furan-3-yl |
| 7-8 | 2-fluorophenyl |
| 7-9 | 3-fluorophenyl |
| 7-10 | 4-fluorophenyl |
| 7-11 | 2,6-difluorophenyl |
| 7-12 | 3,4-difluorophenyl |
| 7-13 | 3,5-difluorophenyl |
| 7-14 | 4-trifluoromethylphenyl |
| 7-15 | 5-methylfuran-2-yl |
| 7-16 | pyridin-2-yl |
| 7-17 | —(CH$_2$)$_2$-phenyl |
| 7-18 | —CH$_2$-phenyl |

(7-1) (R)-cyclopentylhydroxyphenylacetic acid 1-(N-benzylcarbamimidoyl)-pyrrolidin-3-yl ester. MS m/z: [M+H]$^+$calcd for $C_{25}H_{31}N_3O_3$, 422.24. found 422.4.

(7-2) (R)-cyclopentylhydroxyphenylacetic acid (R)-1-(N-thiophen-2-ylmethyl-carbamimidoyl)pyrrolidin-3-yl ester. MS m/z: [M+H]$^+$calcd for $C_{23}H_{29}N_3O_3S$, 428.19. found 428.4.

(7-3) (R)-cyclopentylhydroxyphenylacetic acid (R)-1-[N-(2-hydroxybenzyl)-carbamimidoyl]pyrrolidin-3-yl ester. MS m/z: [M+H]$^+$calcd for $C_{25}H_{31}N_3O_4$, 438.23. found 438.5.

(7-4) (R)-cyclopentylhydroxyphenyl acetic acid (R)-1-[N-(3-hydroxybenzyl)-carbamimidoyl]pyrrolidin-3-yl ester. MS m/z: [M+H]$^+$calcd for $C_{25}H_{31}N_3O_4$, 438.23. found 438.5.

(7-5) (R)-cyclopentylhydroxyphenylacetic acid (R)-1-[N-(4-hydroxybenzyl)-carbamimidoyl]pyrrolidin-3-yl ester. MS m/z: [M+H]$^+$calcd for $C_{25}H_{31}N_3O_4$, 438.23. found 438.3.

(7-6) (R)-cyclopentylhydroxyphenylacetic acid (R)-1-(N-furan-2-ylmethyl-carbamimidoyl)pyrrolidin-3-yl ester. MS m/z: [M+H]$^+$calcd for $C_{23}H_{29}N_3O_4$, 412.22. found 412.2.

(7-7) (R)-cyclopentylhydroxyphenylacetic acid (R)-1-(N-furan-3-ylmethyl-carbamimidoyl)pyrrolidin-3-yl ester. MS m/z: [M+H]$^+$calcd for $C_{23}H_{29}N_3O_4$, 412.22. found 412.2.

(7-8) (R)-cyclopentylhydroxyphenylacetic acid (R)-1[N-(2-fluoro-benzyl)-carbamimidoyl]pyrrolidin-3-yl ester MS m/z: [M+H]$^+$calcd for $C_{25}H_{30}FN_3O_3$, 440.23. found 440.3.

(7-9) (R)-cyclopentylhydroxyphenylacetic acid (R)-1-[N-(3-fluoro-benzyl)-carbamimidoyl]pyrrolidin-3-yl ester. MS m/z: [M+H]$^+$calcd for $C_{25}H_{30}FN_3O_3$, 440.23. found 440.4.

(7-10) (R)-cyclopentylhydroxyphenylacetic acid (R)-1-[N-(4-fluorobenzyl)-carbamimidoyl]pyrrolidin-yl ester. MS m/z: [M+H]$^+$calcd for $C_{25}H_{30}FN_3O_3$, 440.23. found 440.4.

(7-11) (R)-cyclopentylhydroxyphenylacetic acid (R)-1-[N-(2,6-difluorobenzyl)-carbamimidoyl]pyrrolidin-3-yl ester. MS m/z: [M+H]$^+$calcd for $C_{25}H_{29}F_2N_3O_3$, 458.22. found 458.2.

(7-12) (R)-cyclopentylhydroxyphenylacetic acid (R)-1-[N-(3,4-difluorobenzyl)-carbamimidoyl]pyrrolidin-3-yl ester. MS m/z: [M+H]$^+$calcd for $C_{25}H_{29}F_2N_3O_3$, 458.22. found 458.2.

(7-13) (R)-cyclopentylhydroxyphenylacetic acid (R)-1-[N-(3,5-difluorobenzyl)-carbamimidoyl]pyrrolidin-3-yl ester. MS m/z: [M+H]$^+$calcd for $C_{25}H_{29}F_2N_3O_3$, 458.22. found 458.2.

(7-14) (R)-cyclopentylhydroxyphenylacetic acid (R)-1-[N-(4-trifluoromethoxybenzyl)-carbamimidoyl]pyrrolidin-3-yl ester. MS m/z: [M+H]$^+$calcd for $C_{26}H_{30}F_3N_3O_4$, 506.22. found 506.2.

(7-15) (R)-cyclopentylhydroxyphenylacetic acid (R)-1-[N-(5-methyl-furan-2-ylmethyl)carbamimidoyl]pyrrolidin-3-yl ester. MS m/z: [M+H]$^+$calcd for $C_{24}H_{31}N_3O_4$, 426.23. found 426.2.

(7-16) (R)-cyclopentylhydroxyphenylacetic acid (R)-1-(N-pyridin-2-ylmethyl-carbamimidoyl)pyrrolidin-3-yl ester. MS m/z: [M+H]$^+$calcd for $C_{24}H_{30}N_4O_3$, 423.23. found 423.2.

(7-17) (R)-cyclopentylhydroxyphenylacetic acid (R)-1-[N-(3-phenylpropyl)-carbamimidoyl]pyrrolidin-3-yl ester. MS m/z: [M+H]$^+$calcd for $C_{27}H_{35}N_3O_3$, 450.27. found 450.2.

(7-18) (R)-cyclopentylhydroxyphenylacetic acid (R)-1-(N-phenethylcarbamimidoyl)-pyrrolidin-3-yl ester. MS m/z: [M+H]$^+$calcd for $C_{26}H_{33}N_3O_3$, 436.25. found 436.2.

Example 8

Following the procedures described in the previous example, and substituting the appropriate starting materials and reagents, compounds 8-1 to 8-13, having the following formula, were also prepared as TFA salts:

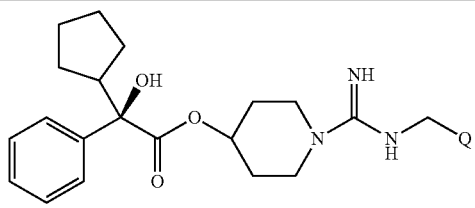

| Ex. | Q |
|---|---|
| 8-1 | phenyl |
| 8-2 | thiophen-2-yl |
| 8-3 | furan-2-yl |
| 8-4 | furan-3-yl |

-continued

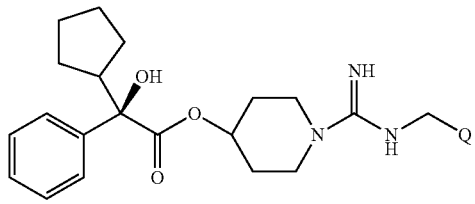

| Ex. | Q |
|---|---|
| 8-5 | 2-hydroxyphenyl |
| 8-6 | 3-hydroxyphenyl |
| 8-7 | 4-hydroxyphenyl |
| 8-8 | 3-methoxyphenyl |
| 8-9 | 2-fluorophenyl |
| 8-10 | 3-fluorophenyl |
| 8-11 | 4-fluorophenyl |
| 8-12 | pyridin-2-yl |
| 8-13 | benzofuran-5-yl |

(8-1) (R)-cyclopentylhydroxyphenylacetic acid 1-(N-benzylcarbamimidoyl)piperidin-4-yl ester. MS m/z: [M+H]$^+$ calcd for $C_{26}H_{33}N_3O_3$, 436.25. found 436.5.

(8-2) (R)-cyclopentylhydroxyphenylacetic acid 1-(N-thiophen-2-ylmethyl-carbamimidoyl)piperidin-4-yl ester. MS m/z: [M+14]$^+$ calcd for $C_{24}H_{31}N_3O_3S$, 442.21. found 442.4.

(8-3) (R)-cyclopentylhydroxyphenylacetic acid 1-(N-furan-2-ylmethyl-carbamimidoyl)piperidin-4-yl ester. MS m/z: [M+H]$^+$ calcd for $C_{24}H_{31}N_3O_4$, 426.23. found 426.2.

(8-4) (R)-cyclopentylhydroxyphenylacetic acid 1-(N-furan-3-ylmethyl-carbamimidoyl)piperidin-4-yl ester. MS m/z: [M+H]$^+$ calcd for $C_{24}H_{31}N_3O_4$, 426.23. found 426.2.

(8-5) (R)-cyclopentylhydroxyphenylacetic acid 1[N-(2-hydroxybenzyl)-carbamimidoyl]piperidin-4-yl ester. MS m/z: [M+H]$^+$ calcd for $C_{26}H_{33}N_3O_4$, 452.25. found 452.2.

(8-6) (R)-cyclopentylhydroxyphenylacetic acid 1-[N-(3-hydroxybenzyl)-carbamimidoyl]piperidin-4-yl ester. MS m/z: [M+H]$^+$ calcd for $C_{26}H_{33}N_3O_4$, 452.25. found 452.2.

(8-7) (R)-cyclopentylhydroxyphenylacetic acid 1-[N-(4-hydroxybenzyl)-carbamimidoyl]piperidin-4-yl ester. MS m/z: [M+H]$^+$ calcd for $C_{26}H_{33}N_3O_4$, 452.25. found 452.2.

(8-8) (R)-cyclopentylhydroxyphenylacetic acid 1-[N-(3-methoxybenzyl)-carbamimidoyl]piperidin-4-yl ester. MS m/z: [M+H]$^+$ calcd for $C_{27}H_{35}N_3O_4$, 466.26. found 466.2.

(8-9) (R)-cyclopentylhydroxyphenylacetic acid 1-[N-(2-fluorobenzyl)-carbamimidoyl]piperidin-4-yl ester. MS m/z: [M+H]$^+$ calcd for $C_{26}H_{32}FN_3O_3$, 454.24. found 454.2.

(8-10) (R)-cyclopentylhydroxyphenylacetic acid 1-[N-(3-fluorobenzyl)-carbamimidoyl]piperidin-4-yl ester. MS m/z: [M+H]$^+$ calcd for $C_{26}H_{32}FN_3O_3$, 454.24. found 454.2.

(8-11) (R)-cyclopentylhydroxyphenylacetic acid 1-[N-(4-fluorobenzyl)-carbamimidoyl]piperidin-4-yl ester. MS m/z: [M+H]$^+$ calcd for $C_{26}H_{32}FN_3O_3$, 454.24. found 454.2.

(8-12) (R)-cyclopentylhydroxyphenylacetic acid 1-(N-pyridin-2-ylmethyl-carbamimidoyl)piperidin-4-yl ester. MS m/z: [M+H]$^+$ calcd for $C_{25}H_{32}N_4O_3$, 437.25. found 437.2.

(8-13) (R)-cyclopentylhydroxyphenylacetic acid 1-(N-benzofuran-5-ylmethyl-carbamimidoyl)piperidin-4-yl ester. MS m/z: [M+H]$^+$ calcd for $C_{28}H_{33}N_3O_4$, 476.25. found 476.4.

Example 9

Following the procedures described in the previous example, and substituting the appropriate starting materials and reagents, (R)-cyclopentylhydroxyphenylacetic acid (R)-1-(N-benzylcarbamimidoyl)piperidin-3-yl ester was also prepared as a TFA salt:

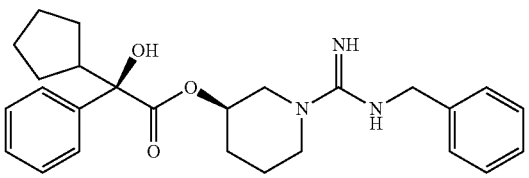

MS m/z: [M+H]$^+$ calcd for $C_{26}H_{33}N_3O_3$, 436.25. found 436.5.

Example 10

Following the procedures described in the previous example, and substituting the appropriate starting materials and reagents, (R)-cyclopentylhydroxyphenylacetic acid 1-[N-(3-phenylpropyl)carbamimidoyl]piperidin-4-yl ester was also prepared as a TFA salt:

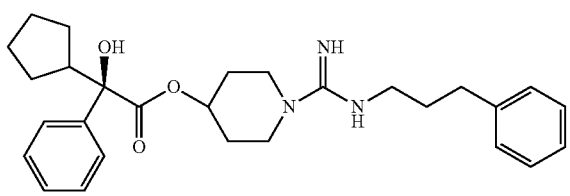

MS m/z: [M+H]$^+$ calcd for $C_{28}H_{37}N_3O_3$, 464.28. found 464.4.

Example 11

Following the procedures described in the previous example, and substituting the appropriate starting materials and reagents, compounds 11-1 and 11-2, having the following formula, were also prepared as TFA salts:

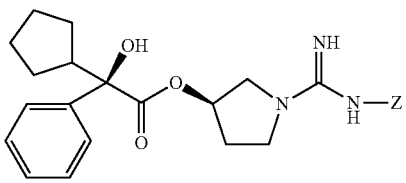

(11-1) (R)-cyclopentylhydroxyphenylacetic acid (R)-1-(N-methylcarbamimidoyl)-pyrrolidin-3-yl ester (Z=—CH$_3$). MS m/z: [M+H]$^+$ calcd for $C_{19}H_{27}N_3O_3$, 346.21. found 346.2.

(11-2) (R)-cyclopentylhydroxyphenylacetic acid (R)-1-(N-butylcarbamimidoyl)-pyrrolidin-3-yl ester (Z=—(CH$_2$)$_3$CH$_3$). MS m/z: [M+H]$^+$ calcd for $C_{22}H_{33}N_3O_3$, 388.25. found 388.2.

Example 12

Following the procedures described in the previous example, and substituting the appropriate starting materials and reagents, (R)-cyclopentylhydroxyphenylacetic acid 1-carbamimidoyl-piperidin-4-yl ester was also prepared as a TFA salt:

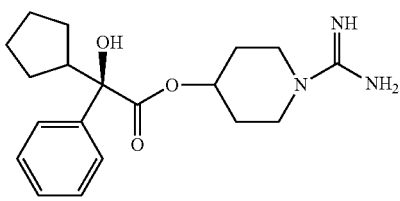

MS m/z: [M+H]$^+$ calcd for $C_{19}H_{27}N_3O_3$, 346.21. found 346.1.

Example 13

Following the procedures described in the previous examples, and substituting the appropriate starting materials and reagents, compounds 13-1 to 13-2, having the following formula, were also prepared as TFA salts:

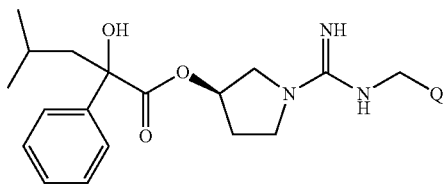

(13-1) 2-hydroxy-4-methyl-2-phenylpentanoic acid (R)-1-(N-benzylcarbamimidoyl)-pyrrolidin-3-yl ester (Q=phenyl). MS m/z: [M+H]$^+$ calcd for $C_{24}H_{31}N_3O_3$, 410.24. found 410.2.
(13-2) 2-hydroxy-4-methyl-2-phenylpentanoic acid (R)-1-[N-(4-hydroxybenzyl)-carbamimidoyl]pyrrolidin-3-yl ester (Q=4-hydroxyphenyl). MS m/z: [M+H]$^+$ calcd for $C_{24}H_{31}N_3O_4$, 426.23. found 426.2.

Example 14

Following the procedures described in the previous examples, and substituting the appropriate starting materials and reagents, compounds 14-1 to 14-4, having the following formula, were also prepared as TFA salts:

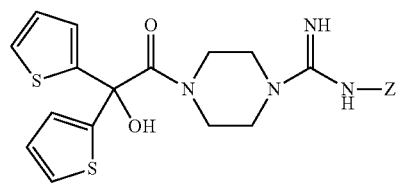

| Ex. | Q |
|---|---|
| 14-1 | phenyl |
| 14-2 | thiophen-2-yl |
| 14-3 | 4-hydroxyphenyl |
| 14-4 | furan-2-yl |

(14-1) N-benzyl-4-(2-hydroxy-2,2-di-thiophen-2-ylacetyl)-piperazine-1-carboxamidine. MS m/z: [M+H]$^+$ calcd for $C_{22}H_{24}N_4O_2S_2$, 441.13. found 441.0.
(14-2) 4-(2-hydroxy-2,2-di-thiophen-2-ylacetyl)-N-thiophen-2-ylmethyl-piperazine-1-carboxamidine. MS m/z: [M+H]$^+$ calcd for $C_{20}H_{22}N_4O_2S_3$, 447.09. found 447.0.

(14-3) N-(4-hydroxybenzyl)-4-(2-hydroxy-2,2-di-thiophen-2-yl-acetyl)-piperazine-1-carboxamidine. MS m/z: [M+H]$^+$ calcd for $C_{22}H_{24}N_4O_3S_2$, 457.13. found 457.0.
(14-4) N-furan-2-ylmethyl-4-(2-hydroxy-2,2-di-thiophen-2-yl-acetyl)-piperazine-1-carboxamidine. MS m/z: [M+H]$^+$ calcd for $C_{20}H_{22}N_4O_3S_2$, 431.11. found 431.0.

Example 15

Following the procedures described in the previous examples, and substituting the appropriate starting materials and reagents, compounds 15-1 to 15-2, having the following formula, were also prepared as TFA salts:

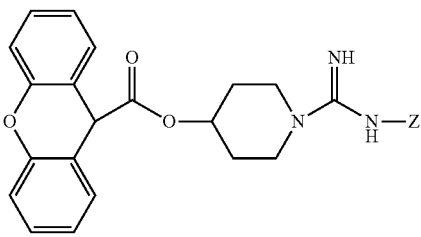

(15-1) 9H-xanthene-9-carboxylic acid 1-[N-(3-phenylpropyl)carbamimidoyl]piperidin-4-yl ester (Z=—(CH$_2$)$_3$-phenyl). MS m/z: [M+H]$^+$ calcd for $C_{29}H_{31}N_3O_3$, 470.24. found 470.4.
(15-2) 9H-xanthene-9-carboxylic acid (R)-1-(N-benzylcarbarnimidoyl)pyrrolidin-3-yl ester (Z=—CH$_2$-phenyl). MS m/z: [M+H]$^+$ calcd for $C_{26}H_{25}N_3O_3$, 428.19. found 428.5.

Example 16

Following the procedures described in the previous examples, and substituting the appropriate starting materials and reagents, 9H-xanthene-9-carboxylic acid (S)-1-carbamimidoylpiperidin-3-ylmethyl ester was also prepared as a TFA salt:

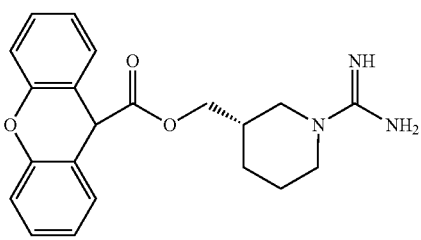

MS m/z: [M+H]$^+$ calcd for $C_{21}H_{23}N_3O_3$, 366.17. found 366.2.

Example 17

Following the procedures described in the previous examples, and substituting the appropriate starting materials and reagents, 9H-xanthene-9-carboxylic acid (R)-1-carbamimidoylpyrrolidin-3-ylmethyl ester was also prepared as a TFA salt:

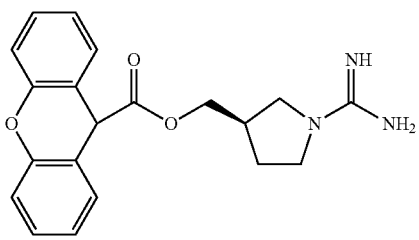

MS m/z: [M+H]+calcd for $C_{20}H_{21}N_3O_3$, 352.16. found 352.2.

Example 18

Following the procedures described in the previous examples, and substituting the appropriate starting materials and reagents, 9H-xanthene-9-carboxylic acid 1-carbamimidoyl-piperidin-4-ylmethyl ester was also prepared as a TFA salt:

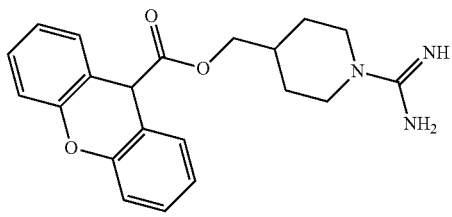

MS m/z: [M+H]+calcd for $C_{21}H_{23}N_3O_3$, 366.17 found 366.2.

Assay 1

Radioligand Binding Assay

Membrane Preparation from Cells Expressing $hM_1$, $hM_2$, $hM_3$ and $hM_4$ Muscarinic Receptor Subtypes CHO cell lines stably expressing cloned human $hM_1$, $hM_2$, $hM_3$ and $hM_4$ muscarinic receptor subtypes, respectively, were grown to near confluency in medium consisting of HAM's F-12 supplemented with 10% FBS and 250 µg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., Journal of Biochemistry 193:265 (1951). All membranes were stored frozen in aliquots at −80° C. or used immediately. Aliquots of prepared $hM_5$ receptor membranes were purchased directly from Perkin Elmer and stored at −80° C. until use.

Radioligand Binding Assay on Muscarinic Receptor

Subtypes $hM_2$, $hM_2$, $hM_3$, $hM_4$ and $hM_5$

Radioligand binding assays were performed in 96-well microtiter plates in a total assay volume of 1000 µL. CHO cell membranes stably expressing either the $hM_1$, $hM_2$, $hM_3$, $hM_4$ or $hM_5$ muscarinic subtype were diluted in assay buffer to the following specific target protein concentrations (µg/well): 10 µg for $hM_1$, 10-15 µg for $hM_2$, 10-20 µg for $hM_3$, 10-20 µg for $hM_4$, and 10-12 µg for $hM_5$. The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 40 µM in dilution buffer and then serially diluted 5× with dilution buffer to final concentrations ranging from 400 fM to 4 µM. The addition order and volumes to the assay plates were as follows: 825 µL assay buffer with 0.1% BSA, 25 µL radioligand, 100 µL diluted test compound, and 50 µmembranes. Assay plates were incubated for 6 hours at 37° C. Binding reactions were terminated by rapid filtration over GF/B glass fiber filter plates (Perkin Elmer Inc., Wellesley, Mass.) pre-treated in 0.3% polyethyleneimine (PEI). Filter plates were rinsed three times with wash buffer (10 mM HEPES) to remove unbound radioactivity. Plates were then air dried, and 50 µL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W. H. Biochemical Pharmacology 22(23):3099-108 (1973)). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. Exemplary compounds of the invention that were tested in this assay, were found to have a $K_i$ value of less than about 100 nM for the $M_3$ muscarinic receptor subtype in this assay. More typically, these compounds were found to have $K_i$ values of less than about 50 nM, with some compounds having $K_i$ values of less than about 10 nM or less than about 1.0 nM.

Assay 2

Muscarinic Receptor Functional Potency Assays

Blockade of Agonist-Mediated Inhibition of cAMP Accumulation

In this assay, the functional potency of a test compound is determined by measuring the ability of the test compound to block oxotremorine-inhibition of forskolin-mediated cAMP accumulation in CHO-K1 cells expressing the $hM_2$ receptor.

cAMP assays are performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells are rinsed once with dPBS and lifted with Trypsin-EDTA solution (0.05% trypsin/0.53 mM EDTA) as described in Assay 1. The detached cells are washed twice by centrifugation at 650×g for five minutes in 50 mLs dPBS. The cell pellet is then re-suspended in 10 mL dPBS, and the cells are counted with a Coulter Z1 Dual Particle Counter (Beckman Coulter, Fullerton, Calif.). The cells are centrifuged again at 650×g for five minutes and re-suspended in stimulation buffer to an assay concentration of $1.6 \times 10^6$-$2.8 \times 10^6$ cells/mL.

The test compound is initially dissolved to a concentration of 400 μM in dilution buffer (dPBS supplemented with 1 mg/mL BSA (0.1%)), and then serially diluted with dilution buffer to final molar concentrations ranging from 100 μM to 0.1 nM. Oxotremorine is diluted in a similar manner.

To measure oxotremorine inhibition of AC activity, 25 μL forskolin (25 μM final concentration diluted in dPBS), 25 μL diluted oxotremorine, and 50 μL cells are added to agonist assay wells. To measure the ability of a test compound to block oxotremorine-inhibited AC activity, 25 μL forskolin and oxotremorine (25 μM and 5 μM final concentrations, respectively, diluted in dPBS) 25 μL diluted test compound, and 50 μL cells are added to remaining assay wells.

Reactions are incubated for 10 minutes at 37° C. and stopped by addition of 100 μL ice-cold detection buffer. Plates are sealed, incubated overnight at room temperature and counted the next morning on a PerkinElmer TopCount liquid scintillation counter (PerkinElmer Inc., Wellesley, Mass.). The amount of cAMP produced (pmol/well) is calculated based on the counts observed for the samples and cAMP standards, as described in the manufacturer's user manual. Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $EC_{50}$ of the oxotremorine concentration-response curve and the oxotremorine assay concentration as the $K_D$ and [L], respectively. The $K_i$ values are converted to $pK_i$ values to determine the geometric mean and 95% confidence intervals. These summary statistics are then converted back to $K_i$ values for data reporting.

In this assay, a lower $K_i$ value indicates that the test compound has a higher functional activity at the receptor tested. The exemplified compounds of the invention are expected to have a $K_i$ value of less than about 100 nM for blockade of oxotremorine-inhibition of forskolin-mediated cAMP accumulation in CHO-K1 cells expressing the $hM_2$ receptor.

Blockade of Agonist-Mediated [$^{35}$S]GTPγS Binding

In a second functional assay, the functional potency of test compounds can be determined by measuring the ability of the compounds to block oxotremorine-stimulated [$^{35}$S]GTPγS binding in CHO-K1 cells expressing the $hM_2$ receptor.

At the time of use, frozen membranes are thawed and then diluted in assay buffer with a final target tissue concentration of 5-10 μg protein per well. The membranes are briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine is determined in each experiment.

To determine the ability of a test compound to inhibit oxotremorine-stimulated [$^{35}$S]GTPγS binding, the following is added to each well of 96 well plates: 25 μL of assay buffer with [$^{35}$S]GTPγS (0.4 nM), 25 μL of oxotremorine ($EC_{90}$) and GDP (3 μM), 25 μL of diluted test compound and 25 μL CHO cell membranes expressing the $hM_2$ receptor. The assay plates are then incubated at 37° C. for 60 minutes. The assay plates are filtered over 1% BSA-pretreated GF/B filters using a PerkinElmer 96-well harvester. The plates are rinsed with ice-cold wash buffer for 3×3 seconds and then air or vacuum dried. Microscint-20 scintillation liquid (50 μL) is added to each well, and each plate is sealed and radioactivity counted on a topcounter (PerkinElmer). Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that the test compound has a higher functional activity at the receptor tested. The exemplified compounds of the invention are expected to have a $K_i$ value of less than about 100 nM for blockade of oxotremorine-stimulated [$^{35}$S]GTPγS binding in CHO-K1 cells expressing the $hM_2$ receptor.

Blockade of Agonist-Mediated Calcium Release via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human $M_1$ and $M_3$, and chimpanzee $M_5$ receptors. Antagonist potency can be determined by the ability of antagonists to inhibit agonist-mediated increases in intracellular calcium.

For FLIPR calcium stimulation assays, CHO cells stably expressing the $hM_1$, $hM_3$ and $cM_5$ receptors are seeded into 96-well FLIPR plates the night before the assay is done. Seeded cells are washed twice by Cellwash (MTX Labsystems, Inc.) with FLIPR buffer (10 mM HEPES, pH 7.4, 2 mM calcium chloride, 2.5 mM probenecid in HBSS without calcium and magnesium) to remove growth media and leaving 50 μL/well of FLIPR buffer. The cells are then incubated with 50 μL/well of 4 μM FLUO-4AM (a 2× solution was made) for 40 minutes at 37° C., 5% carbon dioxide. Following the dye incubation period, cells are washed two times with FLIPR buffer, leaving a final volume of 50 μL/well.

To determine antagonist potency, the dose-dependent stimulation of intracellular $Ca^{2+}$ release for oxotremorine is first determined so that antagonist potency can later be measured against oxotremorine stimulation at an $EC_{90}$ concentration. Cells are first incubated with compound dilution buffer for 20 minutes, followed by agonist addition, which is performed by the FLIPR. An $EC_{90}$ value for oxotremorine is generated according to the method detailed in the FLIPR measurement and data reduction section below, in conjunction with the formula $EC_F=((F/100-F)\char`\^1/H)*EC_{50}$. An oxotremorine concentration of $3\times EC_F$ is prepared in stimulation plates such that an $EC_{90}$ concentration of oxotremorine is added to each well in the antagonist inhibition assay plates.

The parameters used for the FLIPR are: exposure length of 0.4 seconds, laser strength of 0.5 watts, excitation wavelength of 488 nm, and emission wavelength of 550 nm. Baseline is determined by measuring the change in fluorescence for 10 seconds prior to addition of agonist. Following agonist stimulation, the FLIPR continuously measures the change of fluorescence every 0.5 to 1 second for 1.5 minutes to capture the maximum fluorescence change.

The change of fluorescence is expressed as maximum fluorescence minus baseline fluorescence for each well. The raw data is analyzed against the logarithm of drug concentration by nonlinear regression with GraphPad Prism (GraphPad Software, Inc., San Diego, Calif.) using the built-in model for sigmoidal dose-response. Antagonist $K_i$ values are determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_i$ value indicates that the test compound has a higher functional activity at the receptor tested. The exemplified compounds of the invention are expected to have a $K_i$ value of less than about 100 nM for blockade of agonist-mediated calcium release in CHO cells stably expressing the $hM_3$ receptor.

Assay 3

Rat Einthoven Assay

This in vivo assay is used to assess the bronchoprotective effects of test compounds exhibiting muscarinic receptor antagonist activity.

All test compounds are diluted in sterile water and are dosed via the inhalation route (IH). The rats (Sprague-Dawley, male, 250-350 g) are exposed to the aerosol generated from an LC Star Nebulizer Set and driven by a mixture of gases (5% $CO_2$/95% atmospheric air). Each test compound solution is nebulized over a 10 minute time period in a pie shaped dosing chamber capable of holding six rats. At predetermined time points after inhalation of compound, the Einthoven assay is performed.

Thirty minutes prior to the start of pulmonary evaluation, the animals are anesthetized with inactin (thiobutabarbital, 120 mg/kg IP). The jugular vein is catheterized with saline filled polyethylene catheters (PE-50) and used to infuse MCh. The trachea is then dissected and cannulated with a 14G needle and used for rat ventilation during pulmonary evaluation. Once surgery is complete, rats are ventilated using a piston respirator set at a stroke volume of 1 ml/100 g body weight but not exceeding 2.5 ml volume, and at a rate of 90 strokes per minute.

The changes in pressure that occur with each breath are measured. Baseline values are collected for at least 2.5 minutes then rats are challenged non-cumulatively with 2-fold incremental increases of the bronchoconstrictor MCh (5, 10, 20, 40 and 80 µg/ml). The MCh is infused for 2.5 minutes from a syringe pump at a rate of 2 mL/kg/min. The animals are euthanized upon completion of the studies.

Changes in ventilation pressure (cm $H_2O$) in treated animals are expressed as % inhibition of MCh response relative to control animals. In this assay, a higher % inhibition value indicates that the test compound has a bronchoprotective effect. Exemplary compounds of the invention that are tested in this assay at a dose of 100 µg/ml are expected to exhibit greater than 35% inhibition, some are expected to exhibit greater than 70% inhibition, and some are expected to exhibit greater than 90% inhibition.

1.5 hr $ID_{50}$ Determination

Standard muscarinic antagonists were evaluated in the rat Einthoven assay 1.5 hrs post-dose. The order of potency ($ID_{50}$s) for the five standards tested was determined to be: ipratropium (4.4 µg/ml)>tiotropium (6 µg/ml)>des-methyl-tiotropium (12 µg/ml)>glycopyrrolate (15 µg/ml)>LAS-34237 (24 µg/ml). The potency of the test compound is similarly determined at 1.5 hrs post-dose.

6 and 24 hr $ID_{50}$ Determination

Standards tiotropium and ipratropium were also evaluated 24 hr and/or 6 hr post-dose in the rat Einthoven assay. Ipratropium (10 and 30 µg/ml) was about 3-fold less potent 6-hr post-dose compared to its 1.5 hr potency. The observed loss of activity at this time point (6 hr) is consistent with its relatively short duration of action in the clinic. Tiotropium showed a slow onset of effect with peak bronchoprotection being achieved 6-hr post-dose. Its 6 hr and 24 hr potency values were not significantly different from each other and were about 2-fold more potent compared to its 1.5 hr potency. The onset of action of the test compound, as well as the 6 and 24 hr potency values, is similarly determined.

Assay 4

Rat Antisialagogue Assay

Rats (Sprague-Dawley, male, 250-350 g) are dosed, anesthetized and cannulated as described for Assay 3. At predetermined time points and after surgery, animals are placed on their dorsal side at a 20° incline with their head in a downward slope. A pre-weighed gauze pad is inserted in the animal's mouth and the muscarinic agonist pilocarpine (PILO) (3 mg/kg, iv.) is administered. Saliva produced during 10 minutes post-PILO is measured gravimetrically by determining the weight of the gauze pad before and after PILO. Antisialagogue effects are expressed as % inhibition of salivation relative to control animals.

1, 6 and 24 hr $ID_{50}$ Determination

The rat antisialagogue assay was developed to assess systemic exposure and calculate the lung selectivity index (LSI) of test compounds. The standard, tiotropium, was evaluated in this model at 1, 6, and 24 hr post-dose. Tiotropium was found to be most potent at inhibiting pilocarpine-induced salivation 6 hrs post dose. This finding is consistent with the peak effects observed in the Einthoven assay.

This model is a modified version of the procedure described in Rechter, "Estimation of anticholinergic drug effects in mice by antagonism against pilocarpine-induced salivation" *Ata Pharmacol Toxicol* 24:243-254 (1996). The mean weight of saliva in vehicle-treated animals, at each pre-treatment time, is calculated and used to compute % inhibition of salivation, at the corresponding pre-treatment time, at each dose.

Exemplary compounds of the invention that are tested in this assay are expected to exhibit $ID_{50}$ values less than 100 µg/ml (measured at 24 hours), with some compounds expected to exhibit an $ID_{50}$ value less than 30 µg/ml, some less than 20 µg/ml, and some less than 15 µg/ml.

The ratio of the anti-sialagogue $ID_{50}$ to bronchoprotective $ID_{50}$ is used to compute the apparent lung selectivity index of the test compound. Generally, compounds having an apparent lung selectivity index greater than about 5 are preferred.

While the present invention has been described with reference to specific aspects or embodiments thereof, it will be understood by those of ordinary skill in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A pharmaceutical composition comprising a compound selected from a compound selected from 4-((R)-2-cyclopentyl-2-hydroxy-2-phenylacetyl)-N-furan-2-ylmethylpiperazine-1-carboxamidine and 4-((R)-2-cyclopentyl-2-hydroxy-2-phenylacetyl)-N-thiophen-2-ylmethyl-piperazine-1-carboxamidine, or a pharmaceutically acceptable salt thereof; and a pharmaceutically acceptable carrier.

2. The pharmaceutical composition of claim 1, further comprising a second therapeutic agent selected from $β_2$ adrenergic receptor agonists, steroidal anti-inflammatory agents, phosphodiesterase-4 inhibitors, and combinations thereof.

3. The pharmaceutical composition of claim 2, wherein the composition comprises a $β_2$ adrenergic receptor agonist and a steroidal anti-inflammatory agent.

4. A method of treating chronic obstructive pulmonary disease or asthma, comprising administering to a patient a therapeutically effective amount of a compound selected from 4-((R)-2-cyclopentyl-2-hydroxy-2-phenylacetyl)-N-furan-2-ylmethylpiperazine-1-carboxamidine and 4-((R)-2-cyclopentyl-2-hydroxy-2-phenylacetyl)-N-thiophen-2-ylmethyl-piperazine-1-carboxamidine, or a pharmaceutically acceptable salt thereof.

5. A method of producing bronchodilation in a patient, comprising administering to a patient a bronchodilation-producing amount of a compound selected from 4-((R)-2-cyclopentyl-2-hydroxy-2-phenylacetyl)-N-furan-2-ylmethylpiperazine-1-carboxamidine and 4-((R)-2-cyclopentyl-2-hydroxy-2-phenylacetyl)-N-thiophen-2-ylmethyl-piperazine-1-carboxamidine, or a pharmaceutically acceptable salt thereof.

6. The pharmaceutical composition of claim 2, wherein the $β_2$ adrenergic receptor agonist is selected from albuterol, bitolterol, fenoterol, formoterol, indacaterol, isoetharine, levalbuterol, metaproterenol, pirbuterol, salbutamol, salmefamol, salmeterol, terbutaline, and pharmaceutically acceptable salts thereof.

7. The pharmaceutical composition of claim 2, wherein the steroidal anti-inflammatory agent is selected from beclomethasone dipropionate; budesonide; butixocort propionate; 20R-16α,17α-[butylidenebis(oxy)]-6α,9α-difluoro-11β-hydroxy-17β-(methylthio)androsta-4-en-3-one (RPR-106541); ciclesonide; dexamethasone; 6α,9α-difluoro-17α-[(2-furanylcarbonyl)oxy]-11β-hydroxy-16α-methyl-3-oxoandrosta-1,4-diene-17β-carbothioic acid S-fluoromethyl ester; 6α,9α-difluoro-11β-hydroxy-16α-methyl-17α-[(4-methyl-1,3-thiazole-5-carbonyl)oxy]-3-oxoandrosta-1,4-diene-17β-carbothioic acid S-fluoromethyl ester; 6α,9α-difluoro-11β-hydroxy-16α-methyl-3-oxo-17α-propionyloxyandrosta-1,4-diene-17β-carbothioic acid (S)-(2-oxotetrahydrofuran-3S-yl) ester; flunisolide; fluticasone propionate; methyl prednisolone; mometasone furoate; prednisolone; prednisone; rofleponide; ST-126; triamcinolone acetonide; and pharmaceutically acceptable salts thereof.

8. The pharmaceutical composition of claim 1, which is suitable for administration by inhalation.

9. The pharmaceutical composition of claim 8, which is in the form of an aerosol.

10. The pharmaceutical composition of claim 8, which is in the form of a powder.

11. The pharmaceutical composition of claim 8, which is in the form of a solution.

12. The pharmaceutical composition of claim 8, wherein the compound is micronized.

13. The pharmaceutical composition of claim 12, wherein the compound is combined with the carrier to form a suspension.

14. The pharmaceutical composition of claim 13, wherein the carrier is an isotonic aqueous solution.

15. The pharmaceutical composition of claim 12, wherein the compound is combined with the carrier to form a free flowing powder.

16. The pharmaceutical composition of claim 15, wherein the carrier is lactose or starch.

17. The pharmaceutical composition of claim 8, which further comprises a liquefied propellant.

18. The pharmaceutical composition of claim 8, which is administered using a nebulizer inhaler.

19. The pharmaceutical composition of claim 8, which is administered using a metered-dose inhaler.

20. The pharmaceutical composition of claim 8, which is administered using a dry powder inhaler.

* * * * *